US008759014B2

(12) United States Patent
Kammula

(10) Patent No.: US 8,759,014 B2
(45) Date of Patent: Jun. 24, 2014

(54) METHODS OF OBTAINING ANTIGEN-SPECIFIC T CELL POPULATIONS

(75) Inventor: Udai S. Kammula, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 188 days.

(21) Appl. No.: 12/866,919

(22) PCT Filed: Feb. 10, 2009

(86) PCT No.: PCT/US2009/033649
§ 371 (c)(1),
(2), (4) Date: Aug. 17, 2010

(87) PCT Pub. No.: WO2009/102697
PCT Pub. Date: Aug. 20, 2009

(65) Prior Publication Data
US 2010/0322910 A1    Dec. 23, 2010

Related U.S. Application Data

(60) Provisional application No. 61/027,623, filed on Feb. 11, 2008.

(51) Int. Cl.
*G01N 33/567* (2006.01)
*C12N 5/08* (2006.01)

(52) U.S. Cl.
USPC .......................... 435/7.2; 435/372.3; 435/373

(58) Field of Classification Search
None
See application file for complete search history.

(56) References Cited

U.S. PATENT DOCUMENTS

| 5,449,752 | A | 9/1995 | Fujii et al. | |
|---|---|---|---|---|
| 5,750,356 | A | 5/1998 | Spack et al. | |
| 6,218,132 | B1 | 4/2001 | Spack et al. | |
| 8,034,334 | B2 * | 10/2011 | Dudley et al. | 424/93.7 |

FOREIGN PATENT DOCUMENTS

| WO | 97/45735 | 12/1997 |
|---|---|---|
| WO | 2006/026746 | 3/2006 |

OTHER PUBLICATIONS

Dudley et al., *Cancer J.*, 6 (2), 69-77 (2000).
Dudley et al., *J. Clin. Oncol.*, 23 (10), 2346-2357 (2005).
Dudley et al., *J. Immunotherapy*, 24 (4), 363-373 (2001).
Dudley et al., *J. Immunotherapy*, 25 (3), 243-251 (2002).
Dudley et al., *Science*, 298, 850-854 (2002).
Kammula et al., *Analyzing T Cell Resp.*, 275-284 (2005).
Kammula et al., *J. Immunol.*, 163, 6867-6875 (1999).
Kammula et al., *J. Natl. Cancer Inst.*, 92 (16), 1336-1344 (2000).
Kammula et al., *J. Trans. Med.*, 6, 1-14 (2008).
Kawakami et al., *Cancer Sci.*, 95 (10), 784-791 (2004).
Loeb at al., *Hepatology*, 32 (3), 626-629 (2003).
Mackensen et al., *J. Clin. Oncol.*, 24 (31), 5060-5069 (2006).
Morrison et al., *Nucl. Acids Res.*, 34 (18), 1-9 (2006).
Powell et al., *Blood*, 105 (1), 241-250 (2005).
Powell et al., *J. Immunol.*, 177 (9), 6527-6539 (2006).
Provenzano at al., *J. Transl. Med.*, 1 (15), 1-11 (2003).
Rentzsch, *Clin. Cancer Res.*, 9, 4376-4386 (2003).
Ryncarz et al., *J. Clin. Microbiol.*, 37, 1941-1947 (1999).
Therasse et al., *J. Natl. Cancer Inst.*, 92, 205-216 (2000).
Vignard et al., *J. Immunol.*, 175 (7), 4797-4805 (2005).
Yee et al., *Nat. Rev. Cancer*, 2 (6), 409-419 (2002).
Yee et al., *PNAS*, 99(25), 16168-16173 (2002).

* cited by examiner

*Primary Examiner* — Michail Belyavskyi
(74) *Attorney, Agent, or Firm* — Leydig, Voit & Mayer, Ltd.

(57) ABSTRACT

The invention provides a method of obtaining a population of antigen-specific T cells from peripheral blood of a host. An embodiment of the method of the invention comprises (i) dividing PBMCs from peripheral blood of a host into more than one sub-population; (ii) contacting the PBMCs with an antigen and IL-2; (iii) obtaining a sample of PBMCs from each sub-population; (iv) identifying an antigen-reactive sub-population by determining by high throughput quantitative PCR the expression of a factor produced by the PBMCs of each sample; (v) dividing the antigen-reactive sub-population into microcultures; (vi) identifying the antigen-reactive microculture; and (vii) expanding the microculture, thereby obtaining a population of T cells specific for the antigen. The invention also provides a population of T cells obtained by the inventive method, a pharmaceutical composition comprising the same, and a method of treating a disease in a host using the pharmaceutical composition. Related isolating and screening methods are further provided.

19 Claims, 6 Drawing Sheets

US 8,759,014 B2

METHODS OF OBTAINING ANTIGEN-SPECIFIC T CELL POPULATIONS

CROSS-REFERENCE TO RELATED APPLICATIONS

This patent application is a U.S. National Phase of International Patent Application No. PCT/US09/33649, filed Feb. 10, 2009, which claims the benefit of U.S. Provisional Patent Application No. 61/027,623, filed Feb. 11, 2008, which is incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 4,165 Byte ASCII (Text) file named "706700ST25.TXT," created on Jul. 16, 2010.

BACKGROUND OF THE INVENTION

Adoptive immunotherapy with autologous tumor infiltrating lymphocytes (TIL) has been shown to mediate significant tumor regression in ~50% of patients with refractory metastatic melanoma (Dudley et al., Science 298: 850-854 (2002) and Dudley et al., J. Clin. Oncol. 23: 2346-2357 (2005)). However, the isolation of TIL requires invasive surgery, which can lead to post-operative complications and delays in initiating adoptive immunotherapy with TIL.

The use of lymphocytes from peripheral blood (i.e., peripheral blood lymphocytes (PBL) or peripheral blood mononuclear cells (PBMCs)) in adoptive immunotherapy, in place of TIL, has been postulated as having several advantages. For example, procuring tumor reactive PBLs from a blood draw or leukapheresis avoids the need for invasive surgery. Also, the broad repertoire of PBL might allow for the isolation of unique populations of tumor-reactive lymphocytes that are not commonly found in TIL. Finally, the use of PBL might allow for the use of a generalized strategy to obtain tumor-reactive lymphocyte populations from patients, regardless of the diversity of the histology, thereby, expanding the therapeutic relevance of this approach.

A significant obstacle to the use of PBL in adoptive immunotherapy has been the lack of the availability of efficient in vitro methods to rapidly isolate and expand tumor reactive T cell clones from the peripheral repertoire. Many attractive tumor antigens are derived from normal self proteins, and conventional views of immunologic tolerance suggest that T cells reactive against these self antigens are rare in the natural peripheral repertoire and are predominantly of low functional avidity, incapable of recognizing tumor cells.

In view of the foregoing, there is a need for a rapid and efficient method of obtaining a population of antigen-specific T lymphocytes, especially rare antigen-specific T lymphocytes, from the peripheral blood of a host.

BRIEF SUMMARY OF THE INVENTION

The invention provides a rapid and efficient method of obtaining a population of antigen-specific T cells, e.g., rare antigen-specific T cells, from the peripheral blood of a host. The method allows for high throughput screening of bulk PBMCs, and yet is highly sensitive. For example, the method can detect low frequency or rare antigen-specific T cells (e.g., T cells that exist in the peripheral blood at a frequency of about 1 of about $1 \times 10^5$ bulk PBMCs or lower).

An embodiment of the method of the invention comprises (i) dividing peripheral blood mononuclear cells (PBMCs) from peripheral blood of a host into more than one sub-population; (ii) contacting the PBMCs with an antigen and Interleukin-2 (IL-2); (iii) obtaining a sample of the contacted PBMCs from each sub-population; (iv) identifying an antigen-reactive sub-population by determining by high throughput quantitative PCR (HT-qPCR) the expression of a factor produced by the PBMCs of each sample; (v) dividing the antigen-reactive sub-population into microcultures; (vi) identifying an antigen-reactive microculture; and (vii) expanding the microculture, thereby obtaining a population of T cells specific for the antigen.

The invention also provides a population of T cells obtained by the above inventive method and a pharmaceutical composition comprising the same. Further provided by the invention is a method of treating a disease in a host. The method comprises administering to the host a population of antigen-specific T cells.

A method of isolating antigen-specific T cells is furthermore provided by the invention. An embodiment of the method of the invention comprises (i) dividing PBMCs from peripheral blood of a host into more than one sub-population; (ii) contacting the PBMCs with an antigen and IL-2; (iii) obtaining a sample of the contacted PBMCs from each sub-population; (iv) identifying an antigen-reactive sub-population by determining by HT-qPCR the expression of a factor produced by the PBMCs of each sample; (v) dividing the antigen-reactive sub-population into microcultures; and (vi) identifying an antigen-reactive microculture. T cells specific for the antigen are isolated from the peripheral blood upon the inventive method.

The invention moreover provides a method of screening candidate cancer antigen epitopes. An embodiment of the method of the invention comprises (i) dividing PBMCs from peripheral blood of a host into more than one sub-population; (ii) contacting the PBMCs with one or more candidate cancer antigen epitopes and IL-2; (iii) obtaining a sample of the contacted PBMCs from each sub-population; and (iv) identifying an antigen-reactive sub-population by determining by high throughput quantitative PCR (HT-qPCR) the expression of a factor produced by the PBMCs of each sample.

BRIEF DESCRIPTION OF THE SEVERAL VIEWS OF THE DRAWING(S)

FIGS. 3A-3E is a set of graphs of the stimulation index ((SI)=IFN-$\gamma$ mRNA (peptide x)/IFN-$\gamma$ mRNA (HIVpol)) of PBMC from 17 HLA-A2+ melanoma patients which were individually sensitized for 6 days with either 1 µM of FLU M1 peptide (FIG. 3A), MART$_{27\text{-}35}$ (FIG. 3B), gp100$_{209\text{-}217}$ (FIG. 3C), gp100$_{154\text{-}162}$ (FIG. 3D) or no peptide (DMSO; FIG. 3E) in the presence of IL-2 (90 IU/ml) and then assayed for T cell recognition of the sensitizing peptide versus the HIV$_{pol}$ peptide pulsed onto T2 cells as determined by qPCR. (O) represents the SI for each microwell. Bar is median SI value. Shaded area represents range of non-specific reactivity (SI=0.5-2.0).

Figure 4A:
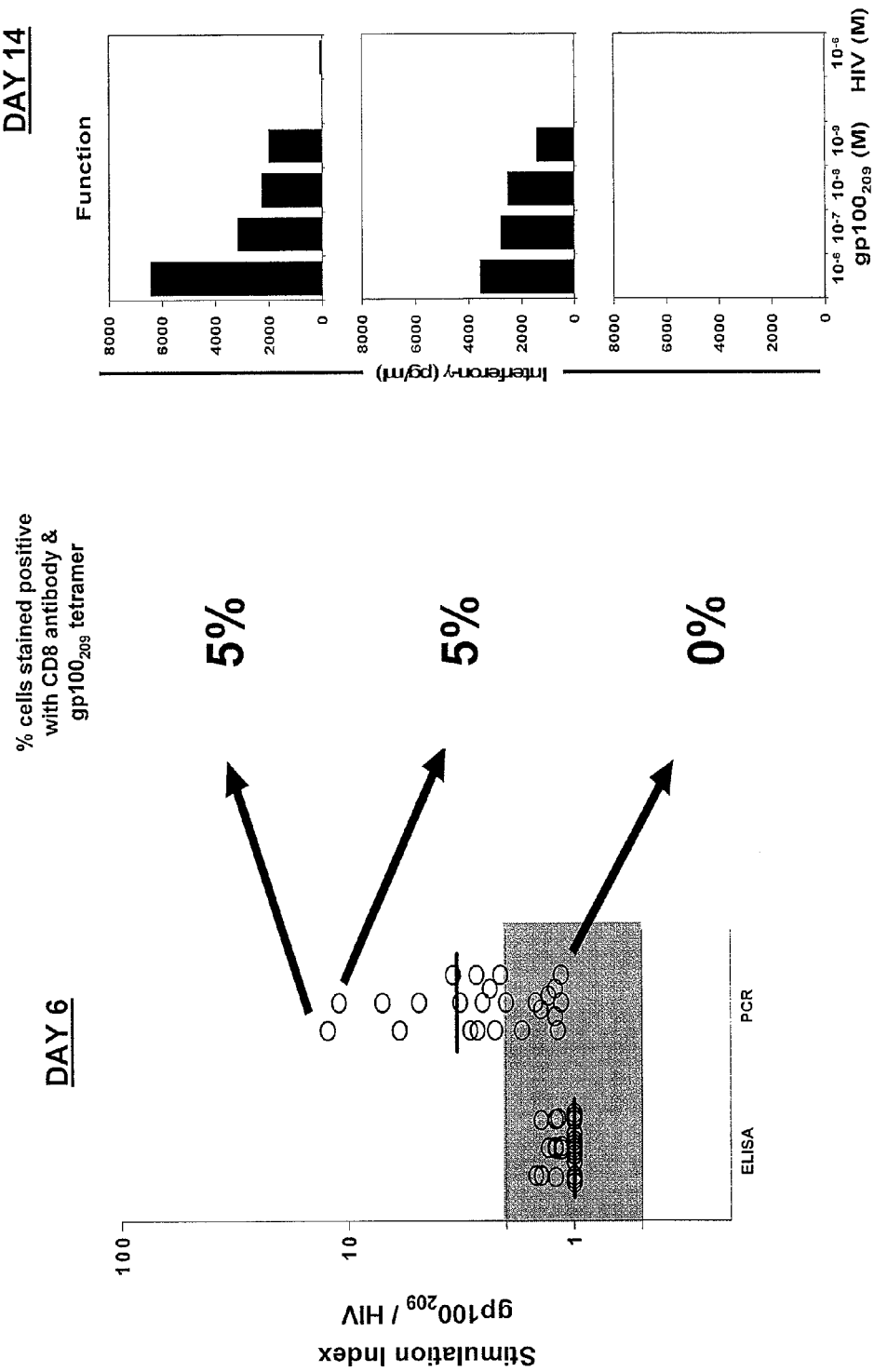

FIG. 4A represents the SI of multiple samples of PBMCs from Patient 1 which were stimulated with gp100$_{209-217}$ peptide for 6 days as determined by ELISA or qPCR (left most panel). (O) represents the SI for each microwell. Shaded area represents range of non-specific reactivity (SI=0.5-2.0). Subpopulations with high or low SI (as determined by qPCR) were selected for rapid expansion. After about 8 days of expansion, the cells were assayed by FACs for percent stained positive for CD8 and gp100$_{209}$ tetramer (middle column). Functional reactivity of the expanded cultures was then assayed by stimulating cells with peptide pulsed T2 cells followed by ELISA measurement of IFN-γ production 24 hours after stimulation. ELISA data represents the average of replicate co-culture wells. (*), not detectable.

Figure 4B:
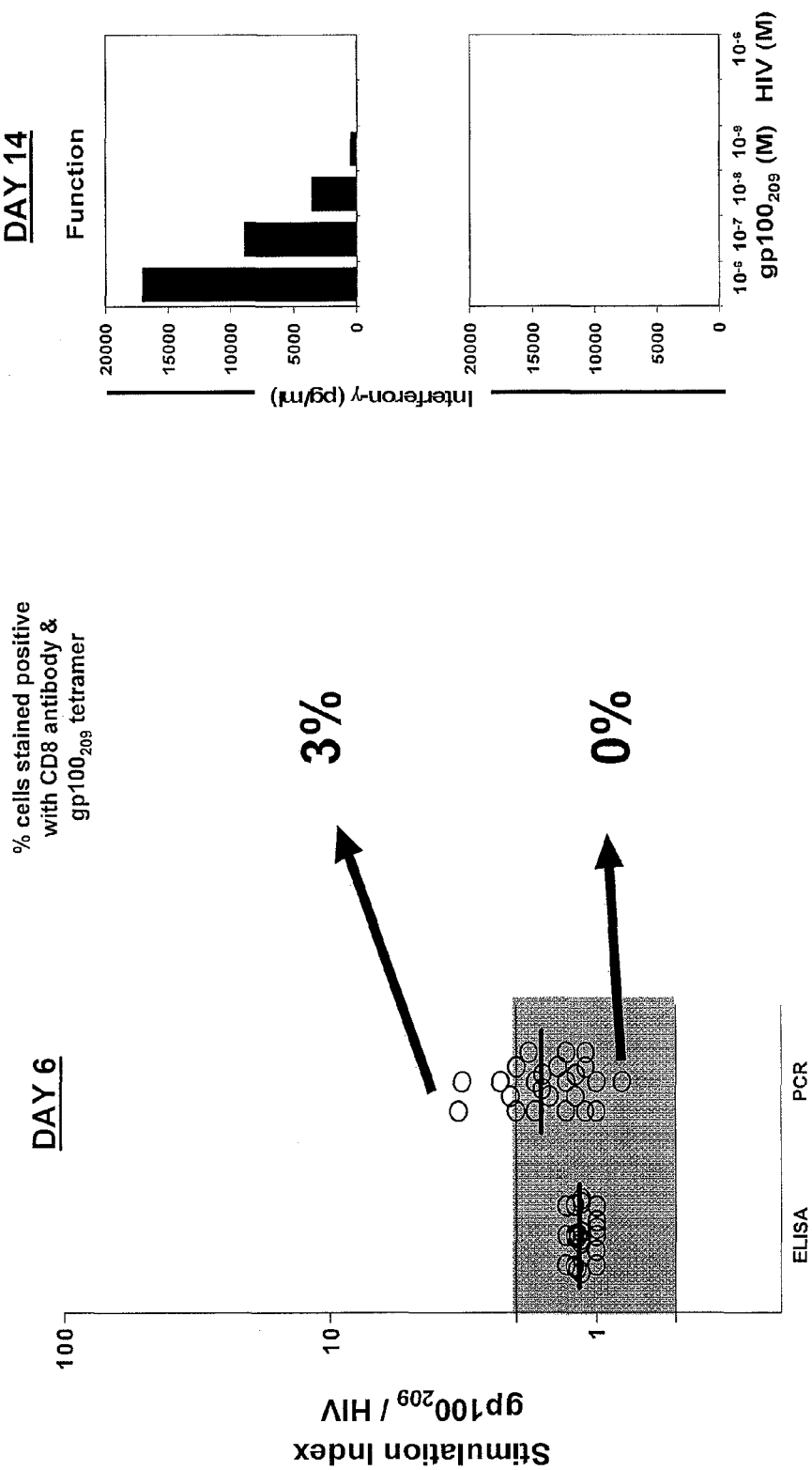

FIG. 4B represents the SI of multiple samples of PBMCs from Patient 3 which were stimulated with gp100$_{209-217}$ peptide for 6 days as determined by ELISA or qPCR (left most panel). (O) represents the SI for each microwell. Shaded area represents range of non-specific reactivity (SI=0.5-2.0). Subpopulations with high or low SI (as determined by qPCR) were selected for rapid expansion. After about 8 days of expansion, the cells were assayed by FACs for percent stained positive for CD8 and gp100$_{209}$ tetramer (middle column). Functional reactivity of the expanded cultures was then assayed by stimulating cells with peptide pulsed T2 cells followed by ELISA measurement of IFN-γ production 24 hours after stimulation. ELISA data represents the average of replicate co-culture wells. (*), not detectable.

DETAILED DESCRIPTION OF THE INVENTION

The invention provides a method of obtaining a population of antigen-specific T cells from the peripheral blood of a host. An embodiment of the method of the invention comprises (i) dividing peripheral blood mononuclear cells (PBMCs) from peripheral blood of a host into more than one sub-population; (ii) contacting the PBMCs with an antigen and Interleukin-2 (IL-2); (iii) obtaining a sample of the contacted PBMCs from each sub-population; (iv) identifying an antigen-reactive sub-population by determining by high throughput quantitative PCR (HT-qPCR) the expression of a factor produced by the PBMCs of each sample; (v) dividing the antigen-reactive sub-population into microcultures; (vi) identifying an antigen-reactive microculture; and (vii) expanding the microculture, thereby obtaining a population of T cells specific for antigen.

Contacting PBMCs from Peripheral Blood

An embodiment of the method of the invention comprises contacting PBMCs from the peripheral blood of a host. The PBMCs of the peripheral blood can be obtained from the host by any suitable means known in the art. For example, the PBMCs can be obtained from the host by a blood draw or a leukapheresis.

The host referred to herein can be any host. Preferably, the host is a mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The PBMCs of the peripheral blood of the host are contacted with an antigen and IL-2 in the method of the invention. By "contact" as used herein refers to providing conditions which promote the antigen and IL-2 to physically contact the PBMCs. Depending on the contacting antigen and the PBMCs contacted with the antigen, one or more PBMCs may be stimulated by the contacting antigen. By "stimulate" as used herein refers to the elicitation of the signal transduction pathways characteristic of an immune response, which signal transduction pathways are initiated by the binding of the T cell receptor (TCR) with the appropriate antigen-MHC complex. The term "stimulate" as used herein is synonymous with "sensitize." Methods of determining whether a T cell is stimulated by an antigen, e.g., the contacting antigen, are known in the art and include, for example, cytokine release assays, e.g., ELISA assays and qPCR assays (such as those described herein in Examples 2 and 3), cytotoxicity assays, and proliferation assays, and the like.

Any antigen can be used to contact the PBMCs. As used herein, the term "antigen" refers to any molecule that can bind specifically to an antibody. For example, the antigen can be any molecule that can be recognized by a T cell in the context of the MHC molecule by which the T cell is restricted. The antigen can be, for example, an antigen which is characteristic of a disease. The disease can be any disease involving an antigen, as discussed herein, e.g., an infectious disease, an autoimmune disease, or a cancer. The antigen could be, for example, a viral antigen, a bacterial antigen, a cancer antigen, etc.

Preferably, the antigen is a cancer antigen or a viral antigen. By "cancer antigen" is meant any molecule (e.g., protein, peptide, lipid, carbohydrate, etc.) solely or predominantly expressed or over-expressed by a tumor cell or cancer cell, such that the antigen is associated with the tumor or cancer. The cancer antigen additionally can be expressed by normal, non-tumor, or non-cancerous cells. However, in such a situation, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen additionally can be expressed by cells of a different state of development or maturation. For instance, the cancer antigen can be additionally expressed by cells of the embryonic or fetal stage, which cells are not normally found in an adult host. Alternatively, the cancer antigen additionally can be expressed by stem cells or precursor cells, which cells are not normally found in an adult host. Another group of cancer antigens are represented by the differentiation antigens that are expressed in only a limited set of tissues in the adult, such as the melanocytes differentiation antigens, whose expression is limited to normal melanocytes. Although it is not known why these molecules elicit immune responses, the limited expression pattern of these proteins may allow these molecules to be recognized by the immune system.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells. In a preferred embodiment of the invention, the cancer antigen is a melanoma cancer antigen or a breast cancer antigen. In a more preferred embodiment, the cancer antigen is selected from the group consisting of gp100, MART-1, NY-ESO-1, a member of the MAGE family of proteins, e.g., MAGE-A1, mesothelin, Tyrosinase, TRP-1, TRP-2, PMSA, Her-2, and p53. In a most preferred embodiment, the cancer antigen is selected from the group consisting of gp 100, NY-ESO-1, and MAGE-1.

Alternatively, the antigen can be a viral antigen. By "viral antigen" is meant those antigens encoded by a part of a viral genome which can be detected by a specific immunological response. Viral antigens include, for example, a viral coat protein, an influenza viral antigen, an HIV antigen, a Hepatitis B antigen, or a Hepatitis C antigen.

With regard to the invention, the antigen can be the whole, full-length, or intact antigen or an immunogenic portion thereof. By "immunogenic portion" as used herein is meant any part of the antigen to which a T cell ceceptor (TCR) specifically binds, such that an immune response is elicited as a result of the TCR binding to the part of the antigen. As used herein, the term "antigen" encompasses the whole, full-length, or intact antigenic protein and any immunogenic portion thereof.

The antigen can be naturally, artificially, synthetically, or recombinantly produced. In this respect, the antigen can be a synthetic, recombinant, isolated, and/or purified protein, polypeptide, or peptide. Methods of making or obtaining such antigens are known in the art. For example, suitable methods of de novo synthesizing polypeptides and proteins (e.g., antigenic polypeptides and proteins) are described in Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwoood et al., Oxford University Press, Oxford, United Kingdom, 2000; and U.S. Pat. No. 5,449,752. Also, polypeptides and proteins (e.g., antigenic polypeptides and proteins) can be recombinantly produced using nucleic acids which encode the polypeptide or protein using standard recombinant methods. See, for instance, Sambrook et al., *Molecular Cloning: A Laboratory Manual*, $3^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. The nucleotide sequences of many antigens are known in the art and are available from the GenBank database of the National Center for Biotechnology Information (NCBI) website. Further, the antigen can be isolated and/or purified from a source, such as a plant, a bacterium, an insect, a mammal, e.g., a rat, a human, etc. Methods of isolation and purification are well-known in the art.

Also, the antigen can be a free antigen, e.g., unbound antigenic peptide (e.g., a free peptide), or can be a bound antigen, e.g., an MHC-peptide tetramer or an antigenic peptide presented by a carrier cell which was pulsed with the peptide. For example, the antigen can be a peptide portion of the antigen gp100, e.g., amino acids 154-162 of gp100 (gp100$_{154-162}$; SEQ ID NO: 2), or a peptide portion of the antigen NY-ESO-1, e.g., amino acids 157-165 of NY-ESO-1 (NY-ESO-1$_{157-165}$; SEQ ID NO: 6). Also, for example, the antigen can be a carrier cell, e.g., T2 cell, which was pulsed with the peptide of SEQ ID NO: 2 or 6.

The PBMCs of the peripheral blood obtained from the host are additionally contacted with IL-2. The IL-2 can be, for example, a recombinantly produced IL-2, such as those that are commercially available from BD Pharmingen, Franklin Lakes, N.J., and BioLegend, San Diego, Calif. The PBMCs can be contacted with any non-toxic dose of IL-2, e.g., a dose which is less than 1000 CU/ml. Preferably, the PBMCs are contacted with an amount of IL-2 ranging from about 10 CU/ml to about 20 CU/ml. More preferably, the PBMCs are stimulated with about 10 CU/ml IL-2.

The PBMCs can be contacted with antigen and IL-2 by any number of suitable means, which means are well-known to those skilled in the art. Strictly by way of example, the PBMCs can be plated into a culture dish containing culture medium comprising the antigen and IL-2. Alternatively, the antigen and IL-2 can be simultaneously or sequentially added to culture medium comprising the PBMCs.

The culture dish containing the PBMCs during contact with the antigen and IL-2 can be any tissue culture plate. As the PBMCs are divided into more than one sub-population before being contacted, the culture dish preferably is a multi-well plate, such as, for example, a 6-, 24-, or 96-well U-bottom plate. In a preferred embodiment, PBMCs from peripheral blood are plated into a 96-well plate comprising culture medium and the antigen and IL-2 are subsequently added to the culture medium comprising the PBMCs.

Any number of PBMCs from peripheral blood can be contacted with the antigen and IL-2. Preferably, a total of about $3 \times 10^5$ PBMCs are contacted among the 96 sub-populations.

Obtaining a Sample

The method of the invention comprises obtaining a sample (e.g., a fraction) of the contacted PBMCs from each sub-population. Preferably, a sample from each sub-population is transferred to a culture dish which is of similar type to the culture dish comprising the contacted PBMCs. For instance, if the contacted PBMCs were contacted in a 96-well plate, then the sample of each sub-population is transferred to a corresponding well of another 96-well plate.

The amount of PBMCs of the sample can be any amount, provided that the sample is only a fraction of the contacted sub-population. Preferably, the sample is about ⅓ of the sub-population of the contacted PBMCs. Advantageously, each sample can comprise as little as about $1 \times 10^5$ PBMCs of the sub-population.

Identifying an Antigen-Reactive Sub-Population

The method of the invention comprises identifying an antigen-reactive sub-population, e.g., a sub-population which comprises one or more PBMCs that react to the contacting antigen or are stimulated by the contacting antigen. The antigen-reactive sub-population is identified by determining the expression of a factor produced by the PBMCs of each sample. The expression of a factor produced by the PBMCs of each sample is determined by high throughput quantitative PCR (HT-qPCR). "High throughput quantitative PCR" as used herein, refers to any of the high throughput quantitative PCR methods known in the art, including, for example, any of those described herein in Example 2, Morrison et al., *Nucleic Acids Research*, e-publication on Sep. 25, 2006; Ryncarz et al., *J. Clin. Microbiol.* 37: 1941-1947 (1999); and Loeb et al., *Hepatology* 32: 626-629 (published on line Dec. 20, 2003). The HT-qPCR may be carried out on any suitable machine appropriately equipped for such assaying. The HT-qPCR machine can be, for example, the ABI Prism® 7900HT Sequence Detection System, which is commercially available from Applied Biosystems, Foster City, Calif.

The high throughput qPCR can comprise the simultaneous analysis of multiple samples of sub-populations. Preferably, the HT-qPCR comprises the simultaneous analysis of at least 20 samples. More preferably, the HT-qPCR comprises the simultaneous analysis of at least 40 samples. Most preferably, the HT-qPCR comprises the simultaneous analysis of at least 75 samples, if not more, e.g., 90, 96, more than 100.

The PCR primers used in the HT-qPCR can be any PCR primers provided that they allow for the amplification of a portion of a nucleic acid encoding the factor. In a preferred embodiment, each of the forward and reverse PCR primers comprises the nucleotide sequence of SEQ ID NOs: 7 and 8, respectively. Also, while the probe used in the HT-qPCR can comprise any suitable nucleotide sequence, the probe preferably comprises the nucleotide sequence of SEQ ID NO: 9.

The factor for which the level of expression is determined through HT-qPCR can be any T cell factor which is produced in response to antigen binding. The factor can be, for example, Interferon-γ (IFN-γ), Granulocyte Macrophage Colony Stimulating Factor (GM-CSF), Tumor Necrosis Factor-α (TNF-α), or Interleukin-2 (IL-2). Preferably, the factor is IFN-γ.

Desirably, immediately before determining the expression of the factor produced by the PBMCs of each sample, the method further comprises an additional contacting of each sample of PBMCs with antigen and optionally IL-2. Methods of contacting PBMCs with antigen and optionally IL-2 are well-known in the art and include any of the methods described herein. Preferably, the contacting antigen is in the form of a peptide antigen presented by a carrier cell, e.g., T2 cell.

As HT-qPCR determines the copy numbers of expressed mRNAs of the factor of the contacted PBMCs, one or more antigen-reactive sub-populations are identified as those with increased copy numbers of the expressed mRNAs of the factor as compared to a negative control, e.g., a sub-population not contacted with an antigen with or without IL-2, a sub-population contacted with DMSO, a sub-population contacted with an irrelevant peptide, e.g., a peptide which is known to go unrecognized by any of the PBMCs.

One or more antigen-reactive sub-populations as identified via HT-qPCR are then divided into microcultures for purposes of limiting dilution cloning. For example, the single sub-population with the highest copy number of the expressed mRNA of the factor can be selected for limiting dilution cloning. Also, for example, the sub-populations exhibiting the top ten highest copy numbers are selected for limiting dilution cloning. Limiting dilution cloning procedures are well-known in the art, and include, methods such as the one described herein in Example 4. Briefly, the number of PBMCs of an identified sub-population is determined and a calculated amount of the sub-population is placed into a calculated volume of medium in a single well of a multi-well tissue culture plate, such that the calculated cell density of the well is about 1 cell per well.

After culturing the microcultures for a sufficient amount of time, e.g., preferably about 2 weeks, each well containing the microcultures are inspected for growth. The inspection can be a visual inspection in which the bottom of the tissue culture plate containing the micro-cultures are visually inspected (with or without a microscope) for cell clusters, which are representative of cell growth.

Growth positive wells are subsequently assayed for antigen-reactivity to identify the wells containing antigen-reactive clones. The antigen-reactivity can be assayed by any suitable means known in the art, including, for instance, the qPCR methodology described herein in Example 2, the ELISA assay described herein in Example 3, or the visual microcytotoxicity assay described herein in Example 4.

Identification of the antigen-reactive microculture allows for the expansion thereof. Any suitable microculture expansion protocol known in the art can be used. Preferably, the microcultures are expanded in accordance with the rapid expansion protocols described herein in Examples 4 and 14.

Nature of the Antigen-Specific T Cells Obtained by the Inventive Method

The method of the invention obtains a population of antigen-specific T cells, e.g., T cells specific for the contacting antigen. As used herein, the term "antigen-specific" refers to a T cell comprising T cell receptors (TCRs) which specifically bind to and immunologically recognize the contacting antigen, such that binding of the TCRs to the contacting antigen elicits an immune response. The TCRs of the antigen-specific T cell, in contrast, do not bind to a control peptide or irrelevant peptide, which are different from the contacting antigen, and thereby do not elicit an immune response.

In a preferred embodiment of the invention, the antigen-specific T cells of the population obtained by the method of the invention are highly avid for the contacting antigen, in that the TCRs expressed on the surface of the T cells strongly and specifically bind to the antigen for which the TCRs are specific, e.g., the contacting antigen. High avidity can be demonstrated by assaying the minimum amount of antigenic peptide pulsed into target cells required for the target cells to be recognized and killed by the T cells. Highly avid T cells can recognize, for example, target cells pulsed with as little as about $10^{-10}$ to about $10^{-11}$ M antigenic peptide.

In one embodiment of the invention, the antigen-specific T cells are specific for a cancer antigen. In this instance, it is preferable for the antigen-specific T cells to recognize tumor cells which express the cancer antigen for which the T cells are specific, e.g., express the contacting antigen. Tumor cell recognition refers to the ability of the T cells to immunologically recognize the antigen and cause killing of the tumor cell. Methods of testing whether T cells recognize tumor cells are well-known in the art and include, for example, the method set forth herein in Example 10.

The antigen-specific T cells of the population obtained by the inventive method can be of any phenotype. Preferably, the T cells of the obtained population are CD27$^+$ (e.g., express the CD27 protein). Additionally, the T cells can have a phenotype which is similar to those described in Examples 6 and 12. In one embodiment of the invention, at least 80% of the antigen-specific T cells of the population obtained by the inventive method are CD27$^+$ T cells.

The antigen-specific T cells can be any T cells, including, but not limited to CD8$^+$ T cells, CD4$^+$ T cells, CD8$^+$/CD4$^+$ T cells, and the like. As the antigen-specific T cells are obtained from bulk PBMCs from peripheral blood, it is understood that the antigen-specific T cells of the population are not tumor infiltrating lymphocytes (TILs), since TILs are not considered to be in the peripheral blood.

Sensitivity

Advantageously, the method is highly sensitive in that low frequency or rare antigen-specific T cells are detected. For example, the inventive method can detect T cells which naturally exist in the peripheral blood at a frequency of about 1 of about $5\times10^4$ PBMCs from peripheral blood (bulk PBMCs) or at an even lower frequency, e.g., about 1 in $10^5$ bulk PBMCs. In contrast, ELISA assays are unable to detect such low frequency T cells.

As used herein, the term "naturally exist" refers to the number of T cells which are present in the peripheral blood of an untreated host, e.g., a host which has not been administered an agent which affects (increases or decreases) the number of T cells in the peripheral blood. An untreated host refers to, for example, a host which has not undergone an adoptive cell transfer procedure and/or has not received a heteroclitic peptide immunization or vaccine within, e.g., 2 weeks, 1 month, 2 months, 3 months, 6 months, 1 year, 5 years, or 10 years, such that the number of T cells in the peripheral blood might increase or decrease. An untreated host can be, for example, a host who has never undergone adoptive cell transfer and/or received a heteroclitic peptide immunization or vaccine. Methods of determining the frequency of a given antigen-specific T cell are known in the art and include, for example, the method set forth herein in Example 5.

While the inventive method can be highly sensitive with regard to the detection of rare or low frequency T cells, as exemplified above, the invention is not limited to just this aspect. Rather, the inventive method can be used to detect and obtain a population of antigen-specific T cells which naturally exist in the peripheral blood at a relatively higher frequency which one of ordinary skill in the art recognizes as having a potential benefit. For example, the method can be used to detect and obtain a population of antigen-specific T cells which naturally exist in the peripheral blood at a frequency which is greater than about 1 of about $1 \times 10^5$ PBMCs.

Rapidity

Also, the method is advantageously rapid, in that a population of antigen-specific T cells, e.g., clinical grade antigen-specific T cells, can be obtained from the peripheral blood of a host in a relatively short period of time. For example, embodiments of the inventive method (comprising (i) to (vii)) can be carried out in less than about 7 weeks, e.g., about 5 to about 6 weeks, such that a population of clinical grade antigen-specific T cells, e.g., clinical grade antigen-specific T cells, is obtained from the peripheral blood of a host in this time frame. Also, for instance, embodiments of the method can be tailored such that (i) to (iv) is carried out within about 1 week. Alternatively or additionally, embodiments of the method can be tailored such that (i) to (vi) is carried out in about 30 days or less.

While the inventive method can be rapid, as exemplified above, the invention is not limited to just this aspect. Rather, the inventive method can occur in a relatively longer period of time of which one of ordinary skill in the art recognizes as having a potential benefit. For example, the method can be carried out in a time frame which is greater than 7 weeks, e.g., 8, 9, 10 or more weeks.

Efficiency

Furthermore, the method is advantageously efficient in that the method is highly sensitive for low frequency, antigen-specific T cells and detects and isolates a clinical grade population of low frequency, antigen-specific T cells in a relatively short period of time. For instance, the number of PBMCs of the antigen-reactive sub-population identified in (iv) can be less than about 10% of the number of the PBMCs of (i) (the starting amount of PBMCs in (i)). That is to say that (i) to (iv) of the inventive method can effectively eliminate greater than about 90% of the PBMCs of (i) (e.g., the starting number of PBMCs). The number of PBMCs of the antigen-reactive sub-population identified in (iv) also can be, for example, less than about 1% of the number of the PBMCs of (i), which is to say that (i) to (iv) of the inventive method can effectively eliminate greater than about 99% of the PBMCs of (i).

The efficiency of the inventive method also can be exemplified by the degree of homogeneity, e.g., the % clonality, of the obtained population of antigen-specific T cells. For example, the method can obtain a population of antigen-specific T cells which is greater than about 90% clonal, e.g., about 93%, about 95%, about 98%, about 99%, or about 100% clonal.

As the inventive method can be efficient, as exemplified above, the invention is not limited to just this aspect. Rather, the inventive method can be tailored to detect less rare antigen-specific T cells, to detect and isolate a population of antigen-specific T cells in a relatively longer period of time, and/or to obtain a less clonal population of antigen-specific T cells of which one of ordinary skill in the art recognizes as having a potential benefit.

Population of Antigen-Specific T Cells and Pharmaceutical Compositions Comprising Same The invention provides a population of antigen-specific T cells which is obtained by the inventive method. By virtue of being obtained by the inventive method, the population of the antigen-specific T cells and the antigen-specific T cells are as described herein. Namely, the population can be oligoclonal or clonal as described above. Also, at least 80% of the population can be $CD27^+$. The T cells can be CD8+ and/or CD4+. The T cells can be specific to any antigen including any of those described herein.

The inventive population of antigen specific T cells is a clinical grade population of antigen specific T cells. The term "clinical grade" is synonymous with "good manufacturing practice grade" and is meant appropriate for human administration per the guidelines set forth by the Food and Drug Administration (FDA). See, for example, 21 C.F.R. Section 606.

Accordingly, the inventive populations of antigen-specific T cells can be formulated into a composition, such as a pharmaceutical composition. In this regard, the invention provides a pharmaceutical composition comprising any of the populations of antigen-specific T cells described herein and a pharmaceutically acceptable carrier. The inventive pharmaceutical compositions containing any of the inventive populations of antigen-specific T cells can comprise more than one type of population of antigen-specific T cells, e.g., a population of gp100-specific T cells along with a population of NY-ESO-1-specific T cells. Alternatively, the pharmaceutical composition can comprise an inventive population of T cells in combination with another pharmaceutically active agent or drug, such as a T cell growth supporting factor, e.g., IL-2.

With respect to pharmaceutical compositions, the pharmaceutically acceptable carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive populations of antigen-specific T cells, as well as by the particular method used to administer the inventive populations of antigen-specific T cells. Accordingly, there are a variety of suitable formulations of the pharmaceutical composition of the invention. In a preferred embodiment of the invention, the pharmaceutical composition is a parenteral formulation or an intravenous formulation.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

The parenteral formulations will typically contain from about 0.5% to about 25% by weight of the inventive material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)). Preferably, when administering cells, e.g., dendritic cells, the cells are administered via injection.

It will be appreciated by one of skill in the art that, in addition to the above-described pharmaceutical compositions, the populations of the invention can be formulated as inclusion complexes, such as cyclodextrin inclusion complexes, or liposomes.

For purposes of the invention, the amount or dose of the inventive pharmaceutical composition administered should be sufficient to effect, e.g., a therapeutic or prophylactic response, in the subject or animal over a reasonable time frame. For example, the dose of the inventive pharmaceutical composition should be sufficient to cause tumor regression, or treat or prevent a disease (e.g., cancer or viral disease in a period of from about 2 hours or longer, e.g., 12 to 24 or more hours, from the time of administration. In certain embodiments, the time period could be even longer. The dose will be determined by the efficacy of the particular inventive pharmaceutical composition and the condition of the animal (e.g., human), as well as the body weight of the animal (e.g., human) to be treated.

Many assays for determining an administered dose are known in the art. For purposes of the invention, an assay, which comprises comparing the extent to which tumors regress, upon administration of a given dose of an inventive pharmaceutical composition to a mammal among a set of mammals of which is each given a different dose of the inventive pharmaceutical composition, could be used to determine a starting dose to be administered to a mammal. The extent to which tumors regress upon administration of a certain dose can be assayed by methods known in the art, including, for instance, the methods described in Therasse et al., *J. Natl. Cancer Inst.* 92: 205-216 (2000).

The dose of the inventive pharmaceutical composition also will be determined by the existence, nature and extent of any adverse side effects that might accompany the administration of a particular inventive pharmaceutical composition. Typically, the attending physician will decide the dosage of the inventive pharmaceutical composition with which to treat each individual patient, taking into consideration a variety of factors, such as age, body weight, general health, diet, sex, inventive material to be administered, route of administration, and the severity of the condition being treated. By way of example and not intending to limit the invention, the dose of the inventive pharmaceutical composition can be about $1 \times 10^9$ cells to about $3 \times 10^{11}$ T cells.

One of ordinary skill in the art will readily appreciate that the inventive pharmaceutical composition of the invention can be modified in any number of ways, such that the therapeutic or prophylactic efficacy of the inventive pharmaceutical compositions is increased through the modification. For instance, the inventive pharmaceutical compositions can be modified to express T cell growth supporting molecules, e.g., IL-2. Such methods of modifying T cells to express IL-2 genes are known in the art.

Method of Treating a Disease

The inventive pharmaceutical compositions comprising the antigen-specific T cell populations can be used in methods of treating a disease. In this regard, the invention provides a method of treating a disease in a host. The method comprises administering to the host any of the pharmaceutical compositions described herein.

The disease can be any disease involving an antigen, e.g., an infectious disease, an autoimmune disease, or a cancer. For purposes herein, "infectious disease" means a disease that can be transmitted from person to person or from organism to organism, and is caused by a microbial agent (e.g., common cold). Infectious diseases are known in the art and include, for example, a viral disease, a bacterial disease, or a parasitic disease, which diseases are caused by a virus, a bacterium, and a parasite, respectively. In this regard, the infectious disease can be, for example, a hepatitis, sexually transmitted diseases (e.g., Chlamydia, gonorrhea), tuberculosis, HIV/AIDS, diphtheria, hepatitis B, hepatitis C, cholera, SARS, the bird flu, and influenza.

For purposes herein, "autoimmune disease" refers to a disease in which the body produces an immunogenic (i.e., immune system) response to some constituent of its own tissue. In other words the immune system loses its ability to recognize some tissue or system within the body as "self" and targets and attacks it as if it were foreign. Autoimmune diseases can be classified into those in which predominantly one organ is affected (e.g., hemolytic anemia and anti-immune thyroiditis), and those in which the autoimmune disease process is diffused through many tissues (e.g., systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

The disease can be a cancer. The cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. Preferably, the cancer is breast cancer, prostate cancer, ovarian cancer, stomach cancer (e.g., gastric adenocarcinoma), colon cancer, liver cancer, melanoma, basal cell carcinoma, rhabdomyosarcoma, or medulloblastoma. Preferably, the cancer is a melanoma, breast cancer, colorectal cancer, esophageal cancer, gastric cancer, non-small cell lung cancer, a sarcoma, pancreatic cancer, mesothelioma, or ovarian cancer.

The term "treat" as used herein does not necessarily imply 100% or complete treatment. Rather, there are varying degrees of treatment of which one of ordinary skill in the art recognizes as having a potential benefit or therapeutic effect. In this respect, the inventive methods can provide any amount of any level of treatment of cancer in a mammal. Furthermore, the treatment provided by the inventive method can include treatment of one or more conditions or symptoms of the disease, e.g., cancer, being treated.

The pharmaceutical composition administered to the host can be any of those described herein. The T cells of the population of the pharmaceutical composition can be allogeneic or autologous to the host. Preferably, the T cells of the pharmaceutical composition are autologous to the host.

Also, the pharmaceutical composition can be administered to the host through any route. Preferably, the pharmaceutical composition is administered to the host via injection or intravenously.

Method of Isolating Antigen Specific T Cells

The invention also provides a method of isolating antigen-specific T cells from peripheral blood of a host. An embodiment of the method of the invention comprises (i) dividing peripheral blood mononuclear cells (PBMCs) from peripheral blood of a host into more than one sub-population; (ii) contacting the PBMCs with an antigen and Interleukin-2 (IL-2); (iii) obtaining a sample of the contacted PBMCs from each sub-population; (iv) identifying an antigen-reactive sub-population by determining by high throughput quantitative PCR (HT-qPCR) the expression of a factor produced by the PBMCs of each sample; (v) dividing the antigen-reactive sub-population into microcultures; and (vi) identifying an antigen-reactive microculture; whereupon T cells specific for the contacting antigen are isolated from the peripheral blood.

The method of isolating antigen-specific T cells from peripheral blood of the invention can be carried out in accordance with any of the embodiments of (i) to (vi) as described herein with regard to the inventive method of obtaining a clinical population of antigen-specific T cells.

Screening Candidate Cancer Antigen Epitopes

The invention further provides a method of screening candidate cancer antigen epitopes. An embodiment of the method of the invention comprises (i) dividing PBMCs from peripheral blood of a host into more than one sub-population; (ii) contacting the PBMCs with one or more candidate cancer antigen epitopes and IL-2; (iii) obtaining a sample of the contacted PBMCs from each sub-population; and (iv) identifying an antigen-reactive sub-population by determining by high throughput quantitative PCR (HT-qPCR) the expression of a factor produced by the PBMCs of each sample.

A cancer antigen epitope is identified when the sub-population which was contacted by the cancer antigen epitope is identified as antigen reactive, e.g., reactive to the contacting antigen. The identification of an antigen-reactive sub-population can comprise a comparison of the expression level of the factor by the sub-population(s) with a positive control sub-population and a negative control sub-population. The positive control sub-population can be, for example, a sub-population stimulated with IL-2 and a known cancer epitope, e.g., $gp100_{154-162}$, whereas the negative control sub-population can be, for example, a sub-population stimulated with IL-2 and a peptide which is known to not be a cancer epitope.

When a cancer antigen epitope is identified, the method can further comprise (v) dividing the antigen-reactive subpopulation into microcultures; (vi) identifying the antigen-reactive microculture; and (vii) expanding the microculture to thereby obtain a population of T cells specific for the cancer antigen epitope.

In yet another embodiment of the inventive method, the method can further comprise assaying the population for tumor reactivity against a tumor cell line, e.g., a tumor cell line expressing the cancer antigen epitope.

In yet another embodiment of the invention, the method can further comprise determining the cancer antigen of which the cancer antigen epitope is a part, thereby identifying a cancer antigen. Methods of determining the cancer antigen of which the cancer antigen epitope is a part are known in the art, and include, for example, performing a BLAST search for the sequence of the epitope and identifying candidate cancer antigens. Cells expressing the candidate cancer antigens can be produced by known methods of engineering and the cells can be assayed for recognition by the T cell clones which recognize the cancer antigen epitope.

The following examples further illustrate the invention but, of course, should not be construed as in any way limiting its scope.

Example 1

This example demonstrates a method of stimulating PBMCs from peripheral blood of a host, which PBMCs are divided into more than one sub-population, with an antigen, or an epitope thereof, and IL-2.

Synthetic peptides are made for in vitro stimulation of PBMCs using a solid phase method on a peptide synthesizer at the Surgery Branch (NCI). The purity of each peptide is confirmed by mass spectrometry and each is resuspended to 1 mg/ml for in vitro use. Peptides of the following sequences are made: $gp100_{209-217}$ (ITDQVPFSV; SEQ ID NO: 1), $gp100_{154-162}$ (KTWGQYWQV; SEQ ID NO: 2), MART-1$_{27-35}$ (AAGIGILTV; SEQ ID NO: 3), HIVpol$_{476-484}$ (ILKEPVHGV SEQ ID NO: 4), and FLU M1$_{58-66}$ (GILGFVFTL SEQ ID NO: 5).

PBMCs obtained by leukapheresis from HLA-A2$^+$ metastatic melanoma patients are in vitro stimulated in accordance with a 6- or 10-day procedure. The 6-day procedure comprises the following: On day 0, cryopreserved PBMCs are thawed, washed twice with CM, and plated in a 96-well plate (3×10$^5$ cells/well; 0.2 mL/well). Plates are incubated at 37° C. in 5% CO$_2$ overnight. On day 1, the sensitizing or stimulating peptide is added to the PBMC culture plate at a final concentration of 1 μg/ml. On day 2, 90 IU/ml recombinant interleukin 2 (IL-2; Chiron Co., Emeryville, Calif.) is added to the cultures. On day 6, the sensitized cultures are assayed for peptide reactivity by either a qPCR assay or ELISA-based cytokine release assay.

The 10-day in vitro stimulation procedure is the same as the 6-day stimulation procedure, except that an additional peptide exposure is performed on day 6, IL-2 (90 IU/ml) is added on day 7, and the cultures are assayed for reactivity on day 10.

Example 2

This example demonstrates a method of identifying an antigen-reactive sub-population by determining by high throughput qPCR the expression of a factor produced by PBMCs.

PBMCs undergo the 6- or 10-day in vitro stimulation as described in Example 1. On the last day of stimulation (Day 6 or Day 10), T2 cells (HLA-A2$^+$ peptide transporter-associated protein deficient T-B hybrid) are pulsed with either a relevant sensitizing (stimulating) peptide or an irrelevant (control) peptide at 1 μg/mlin medium for ~2 hrs at 37° C. T2 cells are washed three times to remove unbound peptide. From each bulk PBMC culture to be assayed, two equal aliquots of cells (each ~50 μA) are removed and incubated in parallel with 3×10$^4$ T2 cells (pulsed with either relevant or irrelevant peptides) in a 0.2-ml volume in individual wells of a 96 well U-bottom tissue culture plate. After 3 hours of incubation, the 96-well plate is spun (900 RPM, 5 minutes), the supernatant is completely discarded, and the cell pellet placed in RLT lysis buffer (Qiagen, Valencia, Calif.).

RNA isolation is performed in a 96-well format using the RNeasy 96 BioRobot 8000 kit (Qiagen). Total RNA for each sample is transcribed into complementary DNA (cDNA) using TaqMan Reverse Transcription Reagants (Applied Biosystems, Foster City, Calif.). Quantitative real-time PCR is performed to determine the copy number for interferon-γ (IFN-γ) mRNA in each sample, as described previously (Kammula et al., *J. Immuol.* 163: 6867-6875 (1999) and Kammula et al., *J. Natl. Cancer Inst.* 92: 1336-1344 (2000)) using the ABI 7500 Fast Real-Time PCR System (Applied Biosystems, Foster City, Calif.). The IFN-γ mRNA levels in response to the relevant peptide is divided by the IFN-γ mRNA levels induced by the irrelevant HIV$_{pol}$ peptide to define a stimulation index (SI) for each parental PBMC culture: SI=IFN-γ (relevant peptide)/IFN-γ (irrelevant peptide (HIV$_{pol}$)). A PBMC sample with a SI>2 is considered as having specific peptide reactivity. All samples analyzed have $C_T$ values less than 35 cycles to ensure the quality of the PBMC samples in the assay.

Example 3

This example demonstrates a method of identifying an antigen-reactive sub-population by determining by a conventional ELISA assay the expression of a factor produced by PBMCs.

PBMC and derived lymphocyte cultures are tested for antigen-specific reactivity in a cytokine release assay using commercially available IFN-γ ELISA kits (Endogen, Pierce, Rockford, Ill.). T2 cells are pulsed with relevant or irrelevant peptide (1 μg/ml) in medium for ~2 hrs at 37° C., followed by washing (three times) before initiation of co-cultures. For these assays, 10$^5$ responder cells (PBL or cloned T cells) and 10$^5$ stimulator cells (T2 cells or tumor lines) are co-incubated in a 0.2-ml volume in individual wells of a 96-well plate. Supernatants are harvested from duplicate wells after 20-24 hours and IFN-γ secretion is measured in culture supernatants, diluted to be within the linear range of the assay. All data from the ELISA-based assays is presented herein as a mean of duplicate samples. Cultures with IFN-γ production greater than 100 pg/ml and twice background are considered as having specific antigen reactivity.

Example 4

This example demonstrates a method of obtaining a population of antigen-specific T cells in accordance with an embodiment of the invention.

PBMCs obtained by leukapheresis from HLA-A2+ metastatic melanoma patients are used to establish 96 independent subpopulations cultured in complete medium (CM) consisting of RPMI 1640 supplemented with 10% heat-inactivated fetal bovine serum, 2 mM L-glutamine (Invitrogen, Carlsbad, Calif.), 50 units/mL penicillin (Invitrogen), 50 μg/mL streptomycin (Invitrogen), 50 μg/mL gentamicin (Invitrogen), 10 mM Hepes (Invitrogen), and 250 ng/mL Amphotericin B (Invitrogen), along with 10% heat-inactivated human AB serum (Gemini Bio-Products, Woodland, Calif.). Each subpopulation is in vitro stimulated with 1 μM of gp100$_{154-162}$ (KTWGQYWQV; SEQ ID NO: 2) for 10 days in the presence of IL-2 (90 IU/ml) as essentially described in Example 1. On day 10, a sample from each subpopulation is screened using a qPCR assay for specific recognition of the gp100$_{154-162}$ peptide versus the HIV$_{pol}$ peptide, as essentially described in Example 2. The SI reactivities for the 96 wells are stratified by their magnitude and the most reactive subpopulations are selected for limiting dilution cloning.

Limiting dilution cloning is carried out by plating between 1 and 5 PBMCs from a reactive subpopulation/well in 96-well U-bottom plates in 0.2 ml complete medium (CM) additionally containing 30 ng/ml ortho-anti-CD3 (Ortho-Biotech, Raritan, N.J.) and 300 IU/ml IL-2 with 5×10$^4$ allogeneic irradiated 4000 rad) PBMCs/well derived from at least 3 different donors. On day 5 and every 3-4 days thereafter, half of the media in each well is replaced with fresh media containing IL-2.

Approximately 2 weeks after initiating limiting dilution cloning of PBMCs from reactive subpopulations, wells are inspected for cell growth. Cell growth positive wells are screened in a cytotoxicity assay to identify clones with cytolytic activity against peptide pulsed T2 cells. Wells are further characterized by assaying IFN-γ secretion in response to limiting concentrations of peptide pulsed onto T2 cells or to antigen positive tumor lines via ELISA.

Selected clones are rapidly expanded with 30 ng/ml ortho-anti-CD3 and 5×10$^6$ irradiated allogeneic PBMCs in upright 25-cm$^2$ flasks as described previously (Dudley et al., *J. Immunother.* 24: 363-373 (1999)). Additional rapid expansions are performed to determine proliferative capacity of clones. Expanded clones are re-evaluated for peptide and tumor recognition and cell surface phenotype by FACS.

Figure 1:
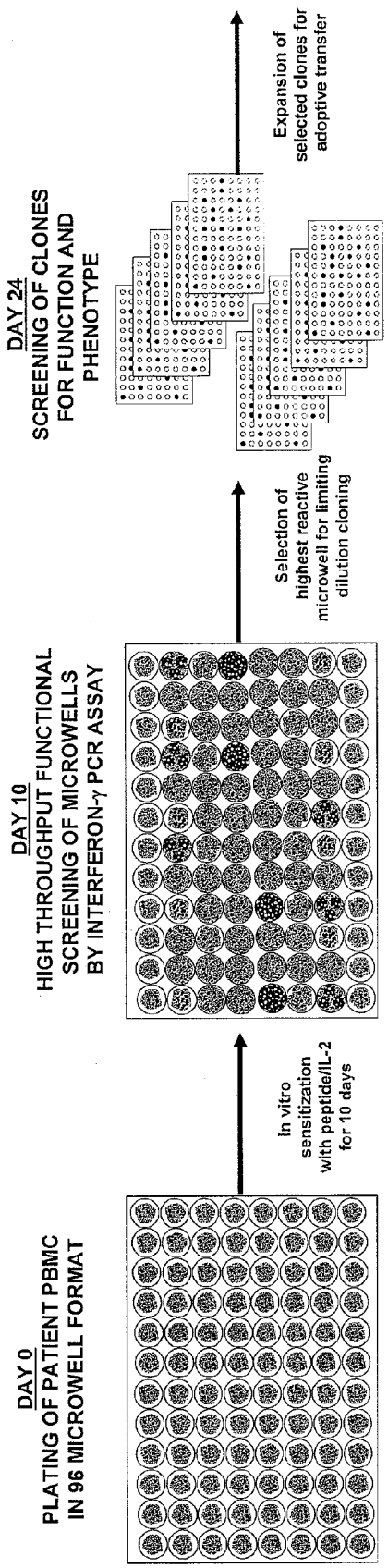
FIG. 1 is a schematic of a method of obtaining a population of antigen-specific T cells for adoptive immunotherapy in accordance with an embodiment of the invention.

The above method of obtaining a population of antigen-specific T cells in accordance with an embodiment of the invention is outlined in FIG. 1.

Example 5

This example demonstrates the biological features of the antigen-specific T cell populations obtained through a method of the invention.

The strategy of Example 4 is applied to PBMC from four melanoma patients (Patients 2, 5, 6, and 7). A sample of the bulk PBMCs from each patient, prior to any in vitro manipulation, undergoes staining with the $gp100_{154-162}$ tetramer to determine natural precursor frequency. The stained cells undergo FACS analysis and it is determined that none of the patients demonstrate a significant population of tetramer positive $CD8^+$ T cells by FACS on day 0, since less than 1% of cells of all four patients were positive for CD8 and $gp100_{154}$ specific T cell receptor (Table 1).

TABLE 1

| Patient | % cells positive for CD8 & $gp100_{154-162}$ expression (Day 0) | Highest SI (Day 10) | % cells positive for CD8 & $gp100_{154-162}$ expression (Day ~25-34) |
|---|---|---|---|
| 2 | <0.5 | 45 | 99 |
| 5 | 0 | 635 | 99 |
| 6 | 0 | 23 | 99 |
| 7 | 0 | 78 | 99 |

After 10 days of sensitization (stimulation) according to the method of Example 1, the 96 independent subpopulations for each patient are screened for peptide reactivity using the qPCR assay. The stratified results for Patients 2, 5, and 6 demonstrate that only 7%, 12%, and 8% of the wells had a SI≥2, respectively; 1%, 3%, and 1% of the wells had a SI≥10, respectively; and the remaining majority of the wells has no detectable peptide reactivity (SI<2). In contrast, for Patient 7, 92% of the wells has a SI≥2 and 60% of the wells has a SI≥10.

The highest reactive subpopulations from patients 2, 5, 6, and 7 (qPCR SI=45, 635, 23, and 78, respectively) are selected for limiting dilution cloning. The frequencies of growth positive clones with lytic ability against peptide pulsed targets are 0.2%, 28%, 0.1%, and 2.3% for Patients 2, 5, 6 and 7 which directly correlate with the qPCR SI ($r^2$=0.99, p<0.0001). These selected clones are expanded with ortho-anti-CD3 and irradiated allogeneic PBMCs as described in Example 4 and undergo FACS analysis between days 25 and 34. FACS analysis with CD8 antibody and $gp100_{154}$ tetramer reveal highly enriched populations (99%) of $gp100_{154-162}$ tetramer positive $CD8^+$ T cells (Table 2). Further, the derived populations are confirmed to be clonal by the sequencing of a single T cell receptor Vβ chain for each patient. The functional avidity of these isolated T cell clones are high, as measured by their ability to recognize $10^{-10}$ to $10^{-11}$ M of $gp100_{154-162}$ peptide pulsed onto T2 cells (Table 1) and HLA $A2^+/gp100^+$ melanoma tumor lines in vitro (Table 3).

TABLE 2

| | $gp100_{154}$ (M) | | | | | | | HIV (M) |
|---|---|---|---|---|---|---|---|---|
| | $10^{-6}$ | $10^{-7}$ | $10^{-8}$ | $10^{-9}$ | $10^{-10}$ | $10^{-11}$ | $10^{-12}$ | $10^{-6}$ |
| Patient 2 clone | 7105 | 6606 | 5102 | 2555 | 187 | <10 | <10 | <10 |
| Patient 5 clone | 12067 | 11274 | 5323 | 1210 | 244 | <10 | <10 | <10 |
| Patient 7 clone | 33349 | 29191 | 26858 | 18575 | 687 | 220 | <10 | <10 |

TABLE 3

| Tumor cell | Mel 526 | Mel 624 | Mel 888 | Hep 3B | Media |
|---|---|---|---|---|---|
| Tumor cell Phenotype | A2+/ gp100+ | A2+/ gp100+ | A2−/gp100+ | A2−/gp100− | na |
| Patient 2 clone | 2724 | 5743 | <10 | <10 | <10 |
| Patient 5 clone | 5114 | 7425 | <10 | <10 | <10 |
| Patient 7 clone | 3975 | 8434 | <10 | <10 | <10 |

$gp100_{154-162}$ $CD8^+$ T cells in 6 of 8 patients (75%) are successfully cloned in this manner. In pilot clinical scale expansions, these clones demonstrated between 850-1000 fold expansions in cell numbers over the initial 14 days after a single rapid expansion in flasks. A second serial expansion of these clones resulted in an additional 400-600 fold expansion over the ensuing week. Thus, two consecutive rapid expansions is sufficient to generate ~$10^{10}$ cells for potential clinical adoptive transfer from each starting isolated clone.

This example demonstrated that the antigen-specific T cell populations obtained through a method of the invention are clonal populations of highly avid T lymphocytes.

Example 6

This example demonstrates the phenotype of the T cell clones obtained in Example 5.

The phenotype of the cells obtained in Example 5 is assessed by cell surface FACS for CD27, CD28, CD45RO, CD45RA, CD62L, and CD25. Specifically, approximately $1\times10^5$ cells are stained in a FACS buffer comprising PBS (BioWhittaker, Walkersville, Md.) and 0.5% BSA with FITC-conjugated monoclonal antibodies specific for CD8, CD25, CD27, CD28, CD45RO, CD45RA, or CD62L (L-selectin) (BD Biosciences, San Jose, Calif.). Immunofluorescence (which is analyzed as the relative log fluorescence of live cells) is then determined using a FACScan flow cytometer (BD Biosciences). A combination of forward angle light scatter and propidium iodide staining is used to gate out dead cells.

As shown in Table 4, the $gp100_{154-162}$ tetramer positive cells from patients 2, 5, and 7 all are uniformly $CD45RO^+$ and $CD62L^-$, consistent with an effector memory phenotype. However, unlike typical antigen experienced T cells, there is persistent variable expression of CD45RA (19-96%). In addition, all of the isolated clones continue to have significant expression of the costimulatory molecule CD27 (90-99%).

This phenotype differs from the TIL derived MART$_{27-35}$ specific clone, JKF6, which has no significant expression of CD27.

TABLE 4

| % Cells positive for staining with antibody specific for: | Patient 2 | Patient 5 | Patient 7 | JKF6 clone (control) |
|---|---|---|---|---|
| CD27 | 99 | 90 | 96 | 5 |
| CD28 | 2 | 6 | 98 | 2 |
| CD45RO | 100 | 100 | 100 | 100 |
| CD45RA | 62 | 19 | 96 | 21 |
| CD62L | 1 | 5 | 13 | 2 |
| CD25 | 1 | 27 | 12 | ND |

Example 7

This example demonstrates the sensitivity of the qPCR assay in comparison to a conventional ELISA assay.

Figure 2:
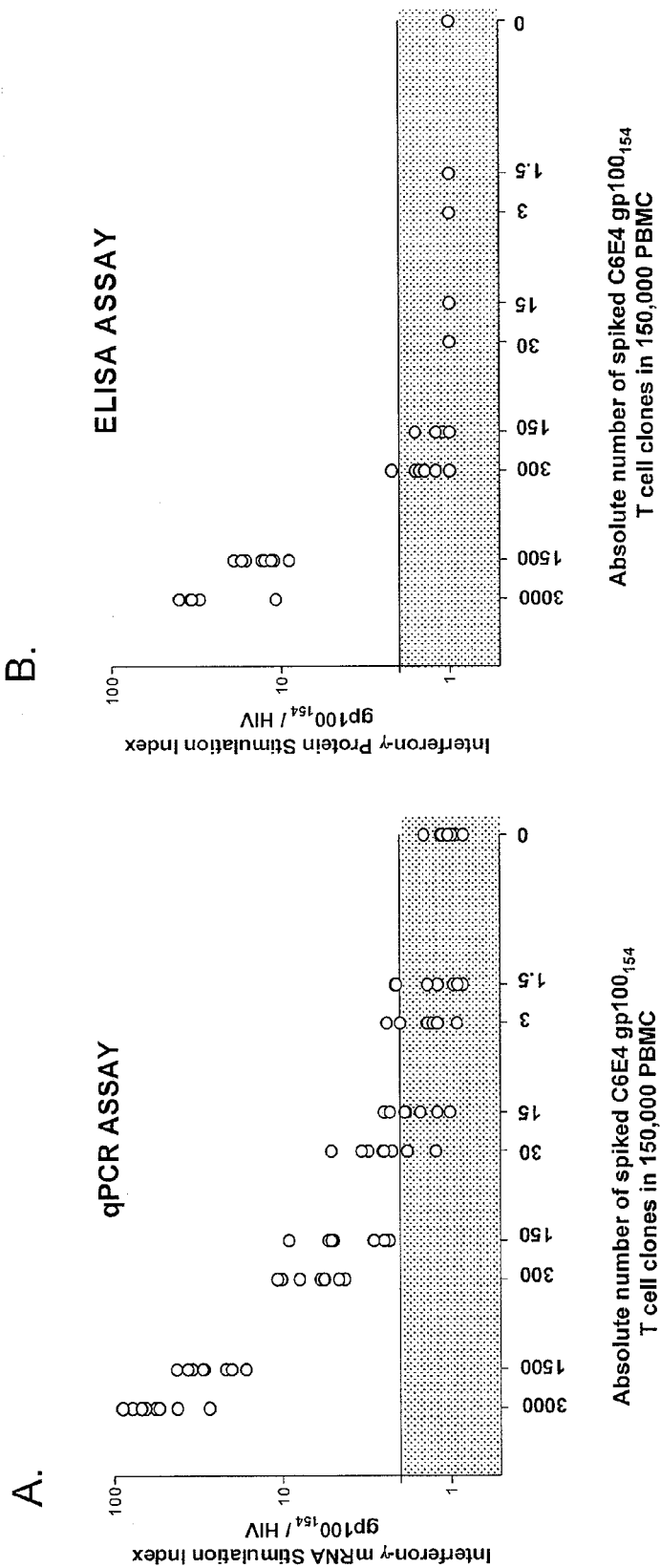
FIG. 2A is a graph of the stimulation index (SI; SI=IFN-$\gamma$ mRNA (gp100$_{154\text{-}162}$)/IFN-$\gamma$ mRNA (HIVpol)) of samples comprising the indicated number of C6E4 gp100$_{154}$ T cell clones spiked into 150,000 PBMC as determined by qPCR.
FIG. 2B is a graph of the stimulation index (SI; SI=IFN-$\gamma$ mRNA (gp100$_{154\text{-}162}$)/IFN-$\gamma$ mRNA (HIVpol)) of samples comprising the indicated number of C6E4 gp100$_{154}$ T cell clones spiked into 150,000 PBMC as determined by ELISA.

Varying absolute numbers (between 1.5 and 3000) of the C6E4 gp100$_{154-162}$ reactive CD8$^+$ T cell clone are spiked into individual microwells of a 96 well plate containing 150,000 nonreactive autologous bulk PBMC populations (FIG. 2). Exogenous cytokines are not added to the PMBC populations and the cells of the populations are not cultured. Rather, the spiked PBMCs are immediately co-incubated with T2 cells pulsed with relevant peptide (gp100$_{154-162}$; 1 µM) or an irrelevant peptide (HIV$_{pol}$; 1 µM). Cellular IFN-γ mRNA production is measured by qPCR at 3 hours after co-incubation, as essentially described in Example 2. Alternatively, supernatant IFN-γ protein production is measured at 24 hours by ELISA, as essentially described in Example 3. Stimulation indexes (SI) for each of the assays are determined by dividing the reactivity against the relevant peptide by the reactivity against the irrelevant peptide (SI=gp100$_{154-162}$/HIV$_{pol}$).

Neither assay demonstrates significant reactivity (gp100$_{154-162}$/HIV$_{pol}$ SI<2) for each of the eight replicate wells without spiked C6E4 clone (PBMC alone). As shown in FIG. 2A, the qPCR assay identifies T cell reactivity in all replicate wells containing between 3000 and 150 spiked clones. For at least 2 of the 8 replicate wells, the qPCR assay can detect reactivity at every dilution down to 1.5 cells spiked into 150,000 PBMC. In contrast, the detection limit for IFN-γ protein ELISA is reached in samples with 300 cells spiked into 150,000 PBMC (FIG. 2B). The qPCR functional assay thus demonstrates a significantly higher sensitivity than the standard ELISA assay, detecting the antigen-induced cytokine response of approximately a single CD8$^+$ T cell at precursor frequency of ~1:100,000 in a 96 microwell format.

This example demonstrated the high sensitivity of the qPCR assay.

Example 8

This example demonstrates that qPCR functional screening rapidly identifies melanoma antigen-specific T cells in short term sensitized (stimulated) peripheral blood cultures.

Figure 3:
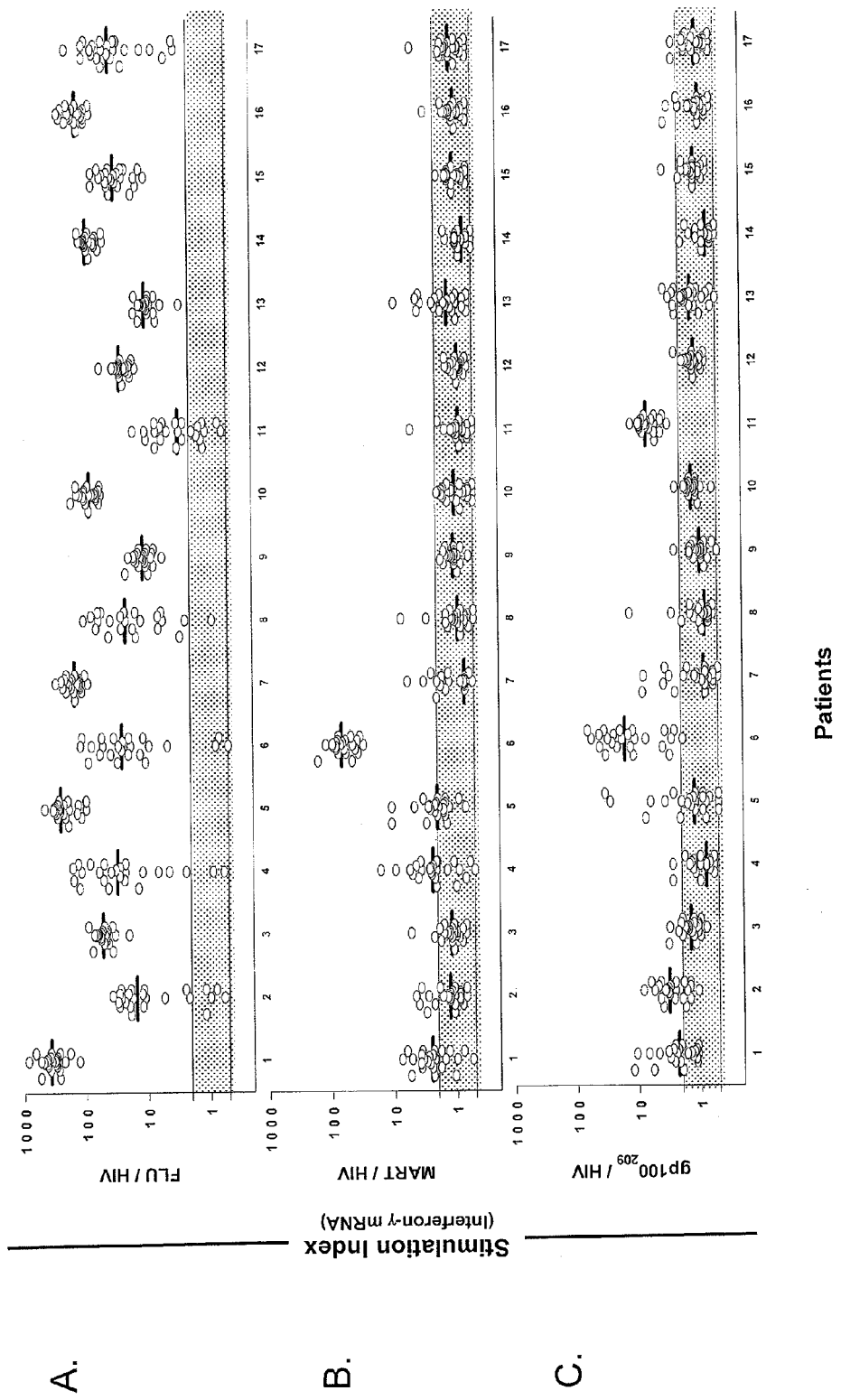
Figure 3:
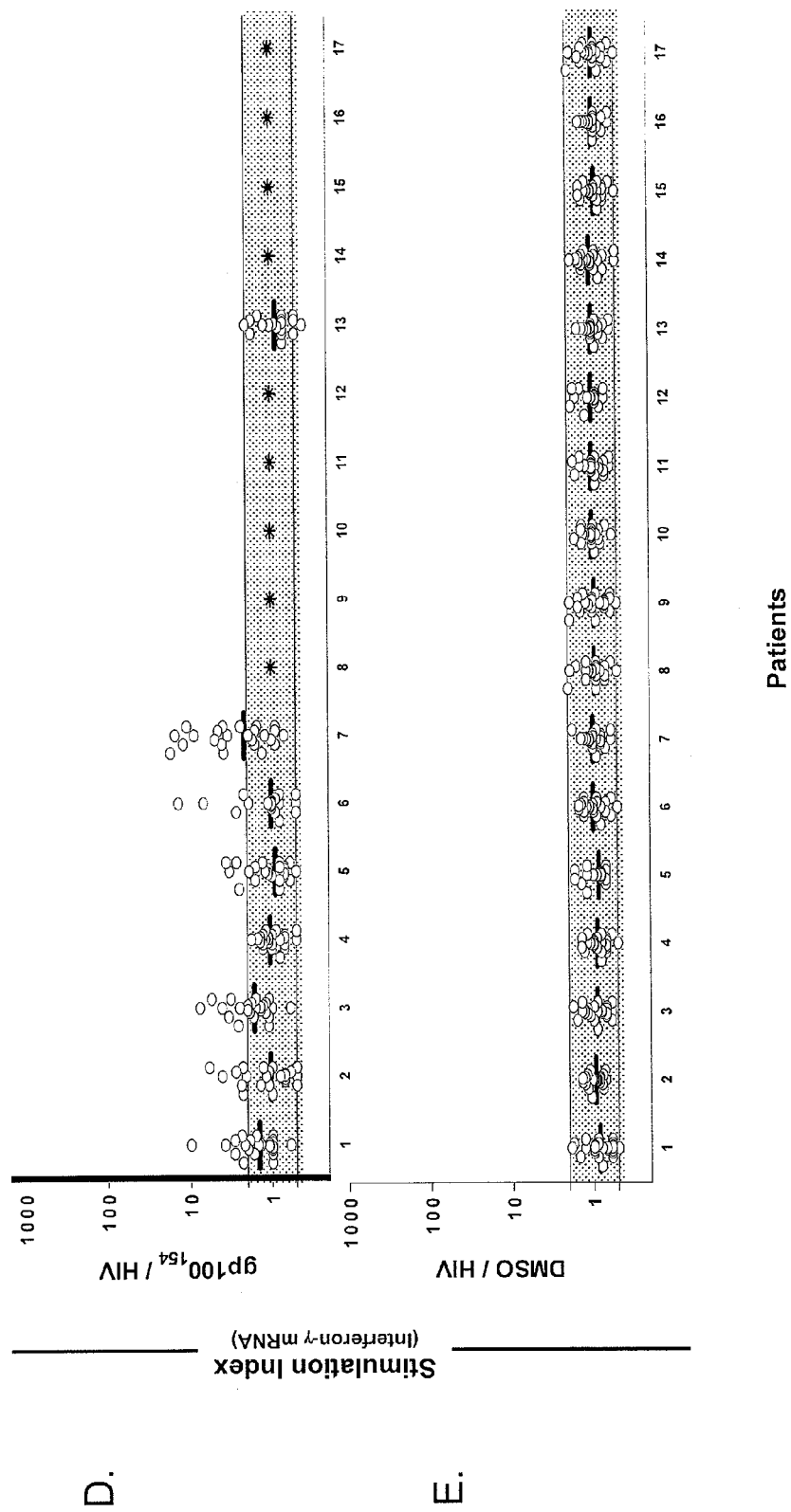

The qPCR assay described in Example 2 is applied to the screening of PBMC for natural CD8$^+$ T cell reactivity against known epitopes from the melanocytic differentiation antigens, gp100 and MART. Peripheral blood leukapheresis samples are obtained from 17 HLA-A2$^+$ metastatic melanoma patients who had not previously undergone antigen specific immunotherapy (i.e., vaccine or cell based transfer therapy). Bulk PBMC from each patient are plated in replicate microwells (n=24) containing ~300,000 cells and individually sensitized (stimulated) for 6 days with 1 µM of FLU M1, MART$_{27-35}$, gp100$_{209-217}$, gp100$_{154-162}$, or no peptide (DMSO) in the presence of IL-2 (90 IU/ml). On day 6, a sample from every microculture (~100,000 cells) is screened using the qPCR assay for recognition of the respective sensitizing peptide versus the irrelevant HIV$_{pol}$ peptide pulsed onto T2 cells (FIG. 3).

The IFN-γ gene expression is normalized as a SI (peptide x/HIV$_{pol}$). The bulk cells cultured in IL-2 with no sensitizing peptide (DMSO alone) are used to define the level of nonspecific background reactivity for each patient (FIG. 3E). The median DMSO/HIV$_{pol}$ SI for all patients is 1.0 (S.D.±0.3) with individual wells ranging from 0.5 to 2.0. By using a cutoff SI value of 2.0, significant microculture reactivity against the FLUM1 peptide in all 17 patients is identified (FIG. 3A), which served as an internal positive control for the sensitization procedure. Variability in the median FLUM1/HIV$_{pol}$ SI of the replicate wells is observed across patients (median range: 3.0 to 376), consistent with varying degrees of natural peripheral blood CD8$^+$ T cell reactivity against the FLU epitope. Further, despite uniform culture conditions, marked well to well variability within the culture replicates is noted for several patients.

Among the cultures sensitized for 6 days with the melanoma antigen epitopes, heterogenic immune reactivity is similarly observed. qPCR analysis of the cultures sensitized with MART$_{27-35}$ (FIG. 3B) revealed three patients (Patients 1, 4, and 6) with median MART/HIV SI well reactivity above 2. However, in 12 patients (70.5%), the qPCR assay identifies at least one individual microculture replicate which met criteria for significant MART peptide reactivity. Similarly, among the gp100$_{209-217}$ sensitized cultures, only 4 patients (Patients 1, 2, 6, and 11) have median culture reactivity >2, but 16 of 17 (94%) patients are found to have individual wells with peptide reactivity above background (FIG. 3C). Among the 8 patients sensitized with the gp100$_{154-162}$ peptide, one patient (patient 7) has median culture reactivity >2, but 6 patients (75%) have individual wells with peptide reactivity (FIG. 3D). In summary, CD8$^+$ T cell reactivity against at least one of the melanoma epitopes is identified in 16 of the 17 patients (94%). It is concluded that the qPCR assay can be used as a highly efficient and rapid screen to detect the reactivity of a variety of melanoma specific T cells in short term sensitized PBMC microcultures.

To determine whether the immune reactivity identified at day 6 by the qPCR assay could also be detected by ELISA, gp100$_{209-217}$ sensitized microcultures from Patients 1 and 3 are evaluated using both assays with an equivalent number of sampled PBMC (~100,000 cells) from each of the replicate wells (FIGS. 4A and B).

ELISA evaluation does not identify any wells from either patient with reactivity above background. In contrast the qPCR assay performed on the same wells demonstrates multiple cultures with detectable peptide reactivity. To confirm that the qPCR reactivity in these early cultures independently correlate with the presence of gp100$_{209-217}$ specific T cells, the microcultures with the highest and lowest SIs are rapidly expanded with anti-CD3, allogeneic feeder cells, and IL-2 over 1 week and evaluated for the presence and activity of gp100$_{209-217}$ reactive CD8$^+$ T cells (FIGS. 4A and B). By day 14, the expanded cultures from the wells with the high SI (Patient 1 SI=11.1 and 12.4; Patient 3 SI=3.3) demonstrate a distinct population of antigen specific CD8$^+$ T cells when stained with the gp100$_{209-217}$ tetramer (3-5% of CD8+ cells). When samples of these expanded cultures are tested for functional recognition of T2 cells pulsed with the gp100$_{209-217}$ peptide, they release significant amounts of interferon-γ protein that is easily detected by ELISA. In contrast, the expanded cultures from the low SI wells (Patient 1 SI=1.1; Patient 3 SI=0.8) have neither discernable tetramer positive cells nor functional activity against peptide pulsed targets.

This example demonstrated that the qPCR assay can be used at an early time point to stratify the epitope reactivity of short term sensitized PBMC microcultures to prospectively identify selected wells enriched for functionally active antigen specific T cells and to eliminate wells with no evidence of reactivity.

Example 9

This example demonstrates a method of detecting NY-ESO$_{157-165}$ specific T cells in the peripheral blood of cancer patients.

PBMC from 9 HLA A2+ melanoma patients and 1 HLA A2+ breast cancer patient are plated in replicate microwells (n=96) containing ~300,000 cells and sensitized (stimulated) for 14 days in the presence of 1 mM of NY-ESO$_{157-165}$ peptide (SLLMWITQC; SEQ ID NO: 6) in the presence of IL-2 (90 IU/ml). On day 14, a sample from every microculture (~100,000 cells) is screened for T cell recognition of T2 cells pulsed with NY-ESO$_{157-165}$ peptide versus a DMSO control using the quantitative RT-PCR assay of Example 2. Cellular IFN-γ mRNA production is measured by qPCR at 3 hours and reported as a stimulation index (SI). SI=IFN-g mRNA (NY-ESO$_{157-165}$)/IFN-g mRNA (DMSO).

NY-ESO$_{157-165}$ specific CD8+ T cell reactivity (SI>2) is detected in individual subpopulations from the peripheral blood of all 9 melanoma patients and in the one patient with breast cancer. Specifically, all 10 patients demonstrate subpopulations with SI>2, 6 of 10 patients demonstrate subpopulations with SI>10, 4 out of 10 patients demonstrated subpopulations with SI>100.

This example demonstrated that the qPCR method could detect NY-ESO$_{157-165}$ specific T cells in the peripheral blood of cancer patients.

Example 10

This example demonstrates another method of obtaining a population of antigen reactive T cells in accordance with an embodiment of the invention.

On Day 0, PBMC from HLA-A2+ cancer patients are stained with NY-ESO$_{157-165}$ tetramers and anti-CD8 to determine natural precursor frequency. PBMC from each patient are plated in replicate microwells (n=96) containing ~300,000 cells and sensitized (stimulated) for 14 days with 1 mM of NY-ESO$_{157-165}$ peptide in the presence of IL-2 (90 IU/ml). On day 14, a sample from every microwell (subpopulation) is screened using the qPCR assay for specific recognition of the NY-ESO$_{157-165}$ peptide versus a DMSO control. The wells with the highest SI reactivity (shown in Table 5) are selected for limiting dilution cloning, which is carried out as essentially described in Example 4. After approximately 2 weeks, growth positive wells are screened for the ability to lyse peptide pulsed T2 cells using a cytotoxicity assay. T cell clones selected on their ability to lyse peptide pulsed T2 cells are rapidly expanded with ortho-anti-CD3 and irradiated allogeneic PBMCs in accordance with Example 4. The clones are stained with NY-ESO$_{157-165}$ tetramer and analyzed via FACS to reveal highly enriched (99%) populations of NY-ESO$_{157-165}$ tetramer-positive CD8+ T cells (Table 5).

TABLE 5

| Patient | Cancer Type | % cells positive for CD8 & NY-ESO$_{157-165}$ expression (Day 0) | Highest SI (Day 14) | % cells positive for CD8 & NY-ESO$_{157-165}$ expression (Day ~30-40) |
|---|---|---|---|---|
| D | melanoma | 0.1 | 7 | 99 |
| F | melanoma | 0.7 | 20 | 99 |
| B | melanoma | 0.4 | 43 | TBD |
| C | melanoma | 0 | 70 | TBD |
| H | melanoma | 0.06 | 79 | TBD |
| J | breast | 1.2 | 288 | TBD |

TBD = to be determined

This example demonstrated that the method of the invention can be successfully obtain clonal populations of NY-ESO-specific, CD8+ T cells.

Example 11

This example demonstrates the biological features of the clonal populations of Example 10.

The functional avidity of the NY-ESO-1-reactive clones of Patient D obtained through Example 10 are assayed for avidity by tumor and peptide-specific stimulation. 1×10$^5$ cloned T cells are co-cultured overnight with an equal number tumor cell lines or T2 cells pulsed with peptide (as specified in Tables 6 and 7), and assessed for IFN-γ (pg/ml) by standard ELISA assay. The results are shown in Tables 6 and 7. Values of 200 pg/ml and twice background are bolded and underlined.

TABLE 6

| | NY-ESO$_{157}$(M) | | | | | | | gp100$_{154}$ M |
|---|---|---|---|---|---|---|---|---|
| | $10^{-6}$ | $10^{-7}$ | $10^{-8}$ | $10^{-9}$ | $10^{-10}$ | $10^{-11}$ | $10^{-12}$ | $10^{-6}$ |
| Frese 9A2 NY-ESO$_{157-165}$ CD8+ Clone | 16,055 | 14,270 | 6,172 | 642 | 11 | 2 | 4 | 2 |
| Frese Cl07 gp 100$_{154-162}$ CD8+ Clone | 0 | 4 | 2 | 24 | 0 | 4 | 20 | 13,770 |
| Media | 0 | 2 | 3 | 1 | 20 | 14 | 1 | 1 |

TABLE 7

| | A2+/NY-ESO+ | | | | | A2+/NY-ESO− | | A2−/NY-ESO− | | |
|---|---|---|---|---|---|---|---|---|---|---|
| | Mel | | | | | | | | | |
| | Mel 1363 | 1300 | Mel 624.38 | H1299-A2 | COSA2:ESO | COSA2:Vector | Panc-1 | Mel 888 | Hep 3B | Media |
| Frese 9A2 NY-ESO$_{157-165}$ CD8+Clone | 5,140 | 1,398 | 830 | 1,191 | 3,911 | 4 | 83 | 2 | 5 | 11 |
| Frese Clo7 gp100154-162 CD8+Clone | 3,494 | 20,900 | 7,161 | 31 | 4 | 5 | 19 | 2 | 3 | 1 |
| Media | 1 | 5 | 4 | 2 | 20 | 25 | 5 | 17 | 2 | 2 |

This example demonstrated that the clones obtained by the inventive method have sufficient avidity to recognize peptide pulsed targets and naturally expressed epitope on tumor cells lines.

Example 12

This example demonstrates the phenotype of the T cell clones obtained in Example 10.

Two clones of Patient D are stained with antibodies specific for CD27, CD28, CD45RO, CD45RA, CD62L, and CD25 and subsequently analyzed via FACS. The results are shown in Table 8.

TABLE 8

| | % clones positive for expression of cell surface marker | | | | | |
|---|---|---|---|---|---|---|
| Patient D | CD27 | CD28 | CD45RO | CD45RA | CD62L | CD25 |
| Clone 9A2 | 66 | 5 | 99.8 | 33 | 3 | 17 |
| Clone 2A11 | 87 | 7 | 99.8 | 34 | 5 | 14 |

This example demonstrated that the clones of Patient D have a phenotype of effector memory, but also are CD27+.

Example 13

This example demonstrates a method of screening candidate cancer antigen epitopes in accordance with an embodiment of the invention.

Mesothelin peptides of the following amino acid sequence are synthesized as essentially described in Example 1: FLLFSLGWV (SEQ ID NO: 12), SLLFLLFSL (SEQ ID NO: 11), NMNGSEYFV (SEQ ID NO: 13), VLPLTVAEV (SEQ ID NO: 14), LIFYKKWEL (SEQ ID NO: 15), LLATQMDRV (SEQ ID NO: 16), LLGFPCAEV (SEQ ID NO: 17), VLLPRLVSC (SEQ ID NO: 18), LPLDLLLFL (SEQ ID NO: 19), and RLSEPPEDL (SEQ ID NO: 20). The peptides are used to contact PBMC sub-populations along with IL-2 in accordance with the procedures described in Example 4. HT-qPCR is performed on a sample of each sub-population to determine the expression of IFN-γ by the contacted PBMC sub-populations.

The highest SI of each PBMC sub-population contacted with the indicated mesothelin peptide is shown in Table 9:

TABLE 9

| Peptide Sequence | SEQ ID NO: | Highest SI (Day 14) |
|---|---|---|
| SLLFLLFSL | 11 | 119 |
| FLLFSLGWV | 12 | 29 |
| NMNGSEYFV | 13 | *<2 |
| VLPLTVAEV | 14 | <2 |
| LIFYKKWEL | 15 | <2 |
| LLATQMDRV | 16 | <2 |
| LLGFPCAEV | 17 | <2 |
| VLLPRLVSC | 18 | <2 |
| LPLDLLLFL | 19 | <2 |
| RLSEPPEDL | 20 | <2 |

*= SI <2, not reactive

The highest mesothelin peptide-reactive sub-populations which recognize SEQ ID NO: 11 and 12 are selected for limiting dilution cloning as essentially described in Example 4.

Cell growth positive wells are screened by assaying IFN-γ secretion in response to varying concentrations of the appropriate antigenic peptide pulsed onto T2 cells. As shown in Table 10, the SLLFLLFSL-reactive clones react to as little as 100 pM of SLLFLLFSL. As shown in Table 11, 6 of the 14 FLLFSLGWV-reactive clones demonstrate reactivity to T2 cells pulsed with as little as 10 pM FLLFSLGWV, whereas all 14 clones exhibit reactivity to T2 cells pulsed with as little as 100 pM FLLFSLGWV.

TABLE 10

| Clone | T2 + Meso 1 uM | T2 + Meso 100 nM | T2 + Meso 10 nM | T2 + Meso 1 nM | T2 + Meso 100 pM | T2 + Meso 10 pM | T2 + Meso 1 pM | T2 + HIV 1 uM |
|---|---|---|---|---|---|---|---|---|
| Clo 2 | 13482 | 13839 | 13108 | 10560 | 3061 | 37 | <10 | <10 |
| Clo 13 | 11511 | 11732 | 11444 | 9371 | 3987 | 71 | <10 | <10 |
| Clo 27 | 9490 | 9363 | 8921 | 3919 | 521 | 12 | <10 | <10 |
| Clo 34 | 3723 | 3885 | 3307 | 2424 | 504 | <10 | <10 | <10 |
| Clo 25 | 12021 | 11877 | 12199 | 10603 | 3664 | 12 | <10 | <10 |
| Clo 28 | 4029 | 4522 | 4598 | 3273 | 632 | <10 | <10 | <10 |

TABLE 10-continued

| Clone | T2 + Meso 1 uM | T2 + Meso 100 nM | T2 + Meso 10 nM | T2 + Meso 1 nM | T2 + Meso 100 pM | T2 + Meso 10 pM | T2 + Meso 1 pM | T2 + HIV 1 uM |
|---|---|---|---|---|---|---|---|---|
| Negative Control | <10 | <10 | <10 | <10 | <10 | <10 | <10 | <10 |
| Media | <10 | <10 | <10 | <10 | <10 | <10 | <10 | <10 |

TABLE 11

| Clone | T2 + Meso 1 uM | T2 + Meso 100 nM | T2 + Meso 10 nM | T2 + Meso 1 nM | T2 + Meso 100 pM | T2 + Meso 10 pM | T2 + Meso 1 pM | T2 + gp154 1 uM | T2 + HIV 1 uM |
|---|---|---|---|---|---|---|---|---|---|
| 2 | 10194 | 10213 | 9640 | 5128 | 1829 | 154 | 0 | 36 | 0 |
| 2p | 18946 | 19294 | 15136 | 9149 | 2775 | 453 | 11 | 11 | 5 |
| 3 | 3877 | 4219 | 3895 | 1493 | 304 | 49 | 0 | 0 | 5 |
| 5 | 8825 | 9466 | 8551 | 4586 | 1381 | 123 | 0 | 0 | 0 |
| 6 | 7904 | 8034 | 7281 | 4007 | 1194 | 86 | 0 | 0 | 0 |
| 6p | 11084 | 10767 | 8377 | 3945 | 1256 | 142 | 5 | 5 | 11 |
| 7 | 10655 | 10225 | 8850 | 4561 | 1063 | 17 | 5 | 17 | 17 |
| 7p | 9173 | 9485 | 9217 | 4953 | 1461 | 217 | 11 | 5 | 5 |
| 11p | 10095 | 10854 | 9136 | 4686 | 1567 | 154 | 5 | 24 | 5 |
| 17 | 11003 | 10674 | 6142 | 2526 | 515 | 17 | 10 | 5 | 0 |
| 20 | 2812 | 3024 | 2694 | 901 | 210 | 42 | 11 | 5 | 0 |
| 21 | 8358 | 8346 | 6790 | 3055 | 571 | 17 | 5 | 5 | 5 |
| 24 | 15585 | 14956 | 10804 | 5109 | 858 | 42 | 10 | 5 | 11 |
| 26 | 8875 | 8906 | 7997 | 4032 | 1107 | 55 | 5 | 0 | 0 |
| Negative control | 36 | 17 | 11 | 5 | 55 | 5 | 5 | 14321 | 0 |
| Media | <10 | <10 | <10 | <10 | <10 | <10 | <10 | <10 | <10 |

The phenotype of Clone 2, which is specific for the mesothelin peptide of SEQ ID NO: 12 is determined by FACS analysis as essentially described in Example 6. As shown in Table 12, the phenotype of the cells is shown to have a moderately differentiated phenotype (CD27$^+$, CD28$^-$, and CD45RA$^+$). Also, 99% of the clones were positive for expression of CD8.

TABLE 12

| | % clones positive for expression of cell surface marker | | | | | |
|---|---|---|---|---|---|---|
| Patient D | CD27 | CD28 | CD45RO | CD45RA | CD62L | CD25 |
| Clone | 81 | 1 | 87 | 99 | 1 | 1 |

This example demonstrates a method of screening candidate cancer antigen epitopes and a method of obtaining a population of mesothelin-reactive T cells.

Example 14

This example demonstrates a method of preparing cells for administration to humans.

Peripheral blood mononuclear cells (PBMC) from patients are obtained by leukopheresis. PBMC are enriched by centrifugation on Lymphocyte separation medium (LSM), (ICN Biomed, Inc; Avrora, Ohio), washed 2 times with Ca$^{++}$—, Mg$^{++}$—, Phenol red-free Hanks' balanced salt solution (HBSS) (BioWhittaker), and cryopreserved at $1\times10^8$ cells/vial in one ml of human serum (Biowhittaker) with 10% DMSO.

One vial of PBMC is thawed by warming rapidly to 37° C. Cells are transferred directly into complete medium (CM), which consists of RPMI-1640 with 10% human serum (Approved source, heat-inactivated 56° C. for 30 minutes) with final concentrations of penicillin G (100 units/ml), streptomycin (100 µg/ml), gentamicin (50 µg/ml), L-glutamine (146 µg/ml, 1 mM). PBMC are washed twice with CM and an aliquot is counted. $1-3\times105$ PBMC are plated in each well of a 96 well flat bottom tissue culture plate in 0.1 ml of CM. Plates are incubated at 37° C. in 5% CO2 overnight to recover from the thaw.

On the following day, hgp100154-162 peptide (NeoMPS, Inc.) is added to the culture plate at a final concentration of 1.0 microgram/ml (approximately 1.0 micromolar). IL-2 is added to each well to 10 CU/ml final concentration on the next day. Four and 5 days later, peptide and IL-2 are added respectively as above.

Between days 10-14 from the date that PMBCs are thawed, an aliquot of cells is removed from each bulk culture well and assayed for activity. Briefly, 50 µl of parental culture is plated per well of a 96 well U-bottom tissue culture plate with $3\times10^4$ T2 cells pulsed with 1.0 micromolar hgp100$_{154-162}$ or T2 pulsed with DMSO. After 3 hours, the co-cultured cells are lysed, RNA isolated and cDNA is synthesized. Quantitative RT-PCR is performed to measure levels of interferon-γ mRNA. The wells that exhibit the highest peptide specificity are selected for subcloning.

Active bulk cultures are cloned by limiting dilution in 96 well U-bottom plates. Briefly, allogeneic PBMC are prepared. PBMC are obtained by thawing frozen leukopheresis vials from normal donors as described above. PBMC are thawed directly into CM, washed twice, resuspended in CM, and then irradiated (340 Gy, Nordion gammacell 1000 Cs137 irradiator. Enough cloning reagents for 40 plates are mixed together: 800 ml CM, $4\times108$ irradiated PBMC (either allogenic or autologous), 30 ng/ml OKT3, and 50 CU/ml IL-2. Responder CTL for subcloning are harvested by removing the entire contents of the most active bulk culture well and adding this to the cloning reagent mixture. These are mixed well and plated in 40 U-bottom plates using a repeating multichannel pipette. Each well is roughly estimated to contain 1 to 4 cells per well. The final components of each well are set forth in Table 13.

TABLE 13

| Component | per well |
|---|---|
| viable cells | 1 to 4 |
| allogeneic or autologous PBMC | $1 \times 10^5$ |
| OKT3 | 30 ng/ml |
| IL-2 | 50 CU/ml |
| CM | 200 microliters |

Wells are screened visually for clonal growth 10-14 days after plating.

Aliquots of all growth positive wells are tested by co-culture assay for specificity and activity. 50 µl aliquots of cells from each well are re-plated in duplicate wells of a 96 well flat bottom plate. $5 \times 10^4$ T2 target cells are added to each well. Typically, one well receives T2 pulsed with hgp100$_{154-162}$ and the other well receives T2 pulsed with a control peptide. After a 24 hr co-incubation period, the co-culture wells are visually screened for specific lysis of the T2 pulsed targets. Wells demonstrating lysis of the hgp100$_{154-162}$ pulsed T2 targets are selected for further expansion.

Each active subclone is expanded using a Rapid Expansion Protocol (REP).

On day 0, autologous or allogeneic PBMC are thawed, washed twice, resuspended in CM and irradiated (340 Gy) as described above. PBMC ($2.5 \times 10^7$) and OKT3 (30 ng/ml) are added to CM (25 ml), mixed well, and aliquots are transferred to tissue culture flasks. Viable CTLs from the well from the limiting dilution cloning procedure (approximately $1 \times 10^5$ cells) are added last. Flasks (25 mm$^2$) are incubated upright at 37° C. in 5% CO$_2$. On day 2, IL-2 is added to 50 CU/ml. On day 5, 20 ml (130 ml for a 175 cm$^2$ flask) of culture supernatant is removed by aspiration (cells are retained on the bottom of the flask). Media is replaced with CM containing 50 CU/ml IL-2. On day 8, an aliquot of cells is removed for counting and re-assay. Cells are assayed for peptide specificity and tumor recognition by co-incubation assay and ELISA. If cell density is greater than $1 \times 10^6$/ml, cells are split into additional flasks or transferred to Baxter 3 liter culture bags. IL-2 is added to 50 CU/ml. Fungizone is added to 1.25 mcg/ml and 1 ml/l Cipro is added. On day 11, IL-2 is added to 50 CU/ml. Cells are split if density exceeds $1.5 \times 10^6$ cells/ml. On day 14, cells are harvested and either prepared for additional REP cycles or cryopreserved.

Cells are tested for activity and specificity by co-culturing with target cells (either tumor cells or T2 cells pulsed with antigenic peptide) followed by measurement of cytokine release via ELISA as described above. The most active clones are expanded further to therapeutic numbers with additional REP cycles. These additional REP cycles are the same as the first REP cycle (described above), except that $1 \times 10^6$ CTLs are added to 75 ml of CM additionally containing AIM V, $2 \times 10^8$ allogeneic or autologous PBMCs, and 30 ng/ml OKT3 in 150 cm$^2$ flasks.

In the REP cycle immediately preceding infusion, Fungizone and Cipro are added on day 8, and AIM V media is used. In general, REP expansion of CTL clones results in 50-200 fold expansion. Thus, at least 2 REP cycles are required to generate sufficient cells for patient treatment. If cells have grown to sufficient numbers for patient treatment, a sample is collected from each flask for microbiology tests 2-3 days before the beginning of CTL therapy (the test takes 2 days). IL-2 is added to 50 CU/ml on day 14 and every 3 days until the final product is prepared for infusion.

On day 14-20, get approval from the clinical team to proceed with the cell harvest. Also, check the quality control tests that are needed before infusion of the cells, as specified in the Certificate of Analysis. The product for infusion is prepared by harvesting and washing the cells in centrifuge tubes or in a continuous centrifuge cell harvester system. Cell cultures in flasks or a small number of Nexell culture bags, are transferred to 250 ml centrifuge tubes. These cells are centrifuged (400×g for 15 min), and then resuspended in HBSS and combined in a single 250 ml tube. With about 4 liters or more of culture fluid in Nexell culture bags, the cells are harvested with the Baxter/Fenwall harvester system, the last step of which is a 2-liter wash with 0.9% sodium chloride. Cells from the continuous centrifuge harvest are transferred from the harvest bag to 250 ml centrifuge tubes. For the last step of both harvesting procedures, cells are centrifuged and resuspended in 100-400 ml of 0.9% sodium chloride containing 1) human albumin (25%) added to a final concentration of 2.5% and 2) recombinant human IL-2 at a final concentration of 50 CU/ml. The cell suspension is then transferred into the infusion bag. The range of cells in the infusion bag is specified in the clinical protocol. Aliquots are taken from the infusion bag for viable cell counting, quality control testing, and cryopreservation of cells. The product is then transferred to the clinical team for infusion as soon as possible.

This example demonstrated a method of preparing cells for administration to humans.

Example 15

This example demonstrates a method of treating cancer with the cells of the invention.

Peripheral blood lymphocytes (approximately $5 \times 10^9$ cells)) are obtained by leukapheresis from patients with metastatic melanoma. Whole PBMC will be cultured in the presence of anti-CD3 (OKT3), aldesleukin (IL-2), and gp100: 154-162 in order to stimulate T-cell growth. Donated whole blood and serum will be provided by volunteers and obtained from the Department of Transfusion Medicine in the NIH Clinical Center. The donated whole blood and serum will be isolated and used in cell culture. In addition, volunteers will undergo apheresis to obtain mononuclear cells which may be used as feeder cells in cell culture. Separate consents will be obtained from all blood and apheresis volunteers.

PBL will be assessed for tumor reactivity as specified in Table 14.

TABLE 14

| Test | Method | Limits | Result | Initials/Date |
|---|---|---|---|---|
| Cell viability[1] | trypan blue exclusion | >70% | | |
| Total viable cell number[1] | visual microscopic count | $\geq 1 \times 10^9$ | | |

TABLE 14-continued

| Test | Method | Limits | Result | Initials/Date |
|---|---|---|---|---|
| Tumor antigen reactivity[2] | γ-IFN release vs A2+/gp100+ tumor cell line | >200 pg/ml | | |
| Microbiological studies | gram stain[1, 3] | no micro-organisms seen | | |
| | aerobic culture[3,4] | no growth | | |
| | fungal culture[3,4] | no growth | | |
| | anaerobic culture[3,4] | no growth | | |
| | mycoplasma test[2] | no growth | | |
| Endotoxin[1] | limulus assay | #5 E.U./kg | | |

[1]Performed on the final product prior to infusion. Results are available at the time of infusion.
[2]Performed 2-10 days prior to infusion (test performed prior to final manipulation). Results are available at the time of infusion.
[3]Performed 2-4 days prior to infusion. Results are available at the time of infusion but may not be definitive.
[4]Sample for test collected on the final product prior to infusion. Results will not be available before cells are infused into the patient.

Cells will be expanded and considered for this trial if they are reactive with the gp100:154-162 melanoma antigen. Once cells have been deemed eligible for use in this trial, patients will be consented on this study and enrolled. The patient must meet an eligibility criteria prior to administration of the preparative regimen. Patients who are otherwise eligible for cell administration but who may not receive high dose aldesleukin because of the presence of cardiovascular or respiratory system medical illnesses will be eligible to receive low dose aldesleukin. Growth and expansion of the final product will be performed after the patient has consented to participate in this specific study. Patients will receive up to $3 \times 10^{11}$ gp100:154-162 reactive PBL. A minimum of approximately $1 \times 10^9$ cells will be given. In prior protocols over $3 \times 10^{11}$ T cells have been safely infused to cancer patients.

Once cells meet the reactivity requirements and are projected to exceed the minimum number specified in Table 9, the patient will receive the lymphocyte depleting preparative regimen consisting of fludarabine and cyclophosphamide, followed by infusion of up to $3 \times 10^{11}$ lymphocytes and the administration of either high-dose aldesleukin or low-dose aldesleukin.

There will be two cohorts of patients depending on eligibility to receive high-dose aldesleukin: 1) patients who are eligible will receive high-dose aldesleukin; and 2) patients who are not eligible to receive high-dose aldesleukin will receive low dose aldesleukin.

Each cohort accrues independently of the other. Patients who are not eligible to receive high-dose aldesleukin will be assigned to receive cells (PBL) plus low-dose subcutaneous (SQ) aldesleukin. The total number of such patients is projected to be too small (<10) to have its own early stopping rule for accrual. Therefore, if accrual ends for the patients who receive high-dose aldesleukin, then no further patients receiving low-dose aldesleukin will be entered. Patients will receive no other experimental agents while on this protocol.

The protocol for drug administration will be as follows:

On Day-7 and -6 at 1 am: Hydrate: Begin hydration with 0.9% Sodium Chloride Injection containing 10 meq/L of potassium chloride at 2.6 ml/kg/hr (starting 11 hours pre-cyclophosphamide and continue hydration until 24 hours after last cyclophosphamide infusion).

On Day-7 and -6 at 11 am: Ondansetron (0.15 mg/kg/dose [rounded to the nearest even mg dose between 8 mg and 16 mg based on patient weight] IV every 8 hours X 3 days) will be given for nausea.

Also, Furosemide 10-20 mg iv will be given.

On Day-7 and -6 at 12 pm (NOON): Cyclophosphamide 60 mg/kg/day X 2 days IV in 250 ml D5W with mesna 15 mg/kg/day X 2 days over 1 hr.

On Day-7 and -6 at 1 pm: Begin to monitor potassium level every 12 hours until hydration is stopped. KCl will be adjusted to maintain serum potassium levels in the normal range.

Also, begin mesna infusion at 3 mg/kg/hour intravenously diluted in a suitable diluent (see pharmaceutical section) over 23 hours after each cyclophosphamide dose.

On Day-5: Stop IV hydration (24 hours after last cyclophosphamide dose). If urine output <1.5 ml/kg/hr, give additional 20 mg furosemide iv. If body weight >2 kg over pre cyclophosphamide value, give additional furosemide 20 mg iv.

On Day-5 to Day-1: Fludarabine 25 mg/m²/day IVPB daily over 30 minutes for 5 days.

Cells are prepared as detailed in Example 14. Cells are delivered to the patient care unit by a staff member from the Tumor Immunology Cell Processing Laboratory. Prior to infusion, the cell product identity label is double-checked by two authorized staff (MD or RN), an identification of the product and documentation of administration are entered in the patient's chart, as is done for blood banking protocols. The cells are to be infused intravenously over 20-30 minutes via non-filtered tubing, gently agitating the bag during infusion to prevent cell clumping.

Day 0 (one to four days after the last dose of fludarabine): gp100:154-162 reactive PBL, from $1 \times 10^9$ up to a maximum of $3 \times 10^{11}$ lymphocytes, will be infused intravenously (i.v.) on the Patient Care Unit over 20 to 30 minutes (between one and four days after the last dose of fludarabine). Cell infusions will be given as an inpatient.

Aldesleukin will be administered as follows: (a) 720,000 IU/kg/dose IV (based on total body weight) over 15 minute every eight hours beginning within 24 hours of cell infusion and continuing for up to 5 days (maximum of 15 doses) or (b) 250,000 IU/kg/day subcutaneously (SQ) daily for five days in the first week and then at a dose of 125,000 IU/kg/day for five days for five weeks (two day break each week).

Day 1-4 (Day 0 is the day of cell infusion) and then as per aldesleukin regimen: Start filgrastim at 10 mcg/kg/day daily on Day 1 or 2 subcutaneously until neutrophil count >1.0× $10^9$/L×3 days or >5.0×$10^9$/L (not to exceed 600 µg/day). Aldesleukin will be administered as follows: (a) 720,000 IU/kg/dose IV (based on total body weight) over 15 minutes every eight hours beginning within 24 hours of cell infusion and continuing for up to 5 days (maximum of 15 doses.) or (b) 250,000 IU/kg/day subcutaneously (SQ) for five days in the first week and then at a dose of 125,000 IU/kg/day for five days for five weeks (two day break each week).

The protocol for drug administration is further depicted in Table 15.

TABLE 15

| Therapy | Day | | | | | | | | | | | |
|---|---|---|---|---|---|---|---|---|---|---|---|---|
| | -7 | -6 | -5 | -4 | -3 | -2 | -1 | 0[1] | 1 | 2 | 3 | 4 |
| Cyclophosphamide 60 mg/kg | X | X | | | | | | | | | | |
| Fludarabine 25 mg/m² | | | X | X | X | X | X | | | | | |
| gp100:154-162 reactive PBL Cells | | | | | | | | X | | | | |
| Aldesleukin[3] | | | | | | | | X[2] | X | X | X | X |
| Filgrastim[4] 10 mcg/kg/day | | | | | | | | | X | X | X | X |
| TMP/SMX[5] 160 mg/800 mg (example) | X | | | | X | | | X | | | | |
| Fluconazole[6] 400 mg po | | | | | | | | | X | X | X | X | X |
| Valacyclovir po or Acyclovir IV[7] | | | | | | | | | X | X | X | X | X |

[1]One to four days after the last dose of fludarabine
[2]Initiate within 24 hours after cell infusion
[3]Aldesleukin will be administered as follows:
720,000 IU/kg/dose IV (based on total body weight) over 15 minute every eight hours beginning within 24 hours of cell infusion and continuing for up to 5 days (maximum of 15 doses.)
250,000 IU/kg/day subcutaneously (SQ) for five days in the first week and then at a dose of 125,000 IU/kg/day for five days for five weeks (two day break each week).
[4]Continue until neutrophils count >1 × 10⁹/L for 3 consecutive days or >5 × 10⁹/L.
[5]The TMP/SMX schedule should be adjusted to QD three times per week (Monday, Wednesday, Friday) and continue for at least six months and until CD4 >200 × 2
[6]Continue until ANC >1000/mm³
[7]In patients positive for HSV, continue until absolute neutrophil count is greater than 1000/mm³

Patients who are eligible to receive high-dose aldesleukin will receive aldesleukin at a dose of 720,000 IU/kg (based on total body weight) as an intravenous bolus over a 15 minute period every eight hours beginning on the day of cell infusion and continuing for up to 5 days (maximum 15 doses). Doses may be skipped depending on patient tolerance. Doses will be skipped if patients reach Grade III or IV toxicity due to aldesleukin except for the reversible Grade III toxicities common to aldesleukin such as diarrhea, nausea, vomiting, hypotension, skin changes, anorexia, mucositis, dysphagia, or constitutional symptoms and laboratory changes. Toxicities will be managed. If these toxicities can be easily reversed within 24 hours by supportive measures then additional doses may be given. Additional instances may arise when in the clinical judgment of the attending physician, based on the extensive clinical experience in the Surgery Branch with aldesleukin, when doses of aldesleukin may be skipped. If greater than 2 doses of aldesleukin are skipped, aldesleukin administration will be stopped. Aldesleukin will be administered as an inpatient.

Patients who are not eligible to receive high-dose aldesleukin will receive low dose aldesleukin at a dose of 250,000 IU/kg subcutaneously daily for 5 days. After a two-day rest, aldesleukin will be administered at a dose of 125,000 IU/kg subcutaneously daily for 5 days for the next five weeks (2 days rest per week). Doses may be skipped depending on patient tolerance. Doses will be skipped if patients reach Grade III or IV toxicity due to low dose aldesleukin except for the reversible Grade III toxicities occurring with low dose aldesleukin such as diarrhea, nausea, vomiting, hypotension, peripheral edema, changes in level of consciousness, infection or laboratory changes. In addition, local inflammation at the injection site with occasional nodular induration has been seen, which is reversible over a period of weeks to months. If the toxicity experienced while receiving low dose aldesleukin is easily reversed by supportive measures, then dosing may continue. Aldesleukin will be administered as an outpatient after the patient or family member have been taught to self-administer the subcutaneous injections.

This example demonstrates a method of treating cancer in humans with the cells of the invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of obtaining a clinical grade population of naturally existing cancer antigen-specific T cells from peripheral blood of a host that has not been treated with an agent which affects T cell numbers in the peripheral blood, comprising:
   (i) dividing peripheral blood mononuclear cells (PBMCs) from peripheral blood of a host into more than one sub-population, wherein the host has not been treated with an agent which affects the number of T cells in the peripheral blood;
   (ii) contacting the PBMCs of each sub-population with a cancer antigen and Interleukin-2 (IL-2);
   (iii) obtaining a sample of the contacted PBMCs from each sub-population;
   (iv) identifying a cancer antigen-reactive sub-population by determining by high throughput quantitative PCR (HT-qPCR) the expression of a factor produced by the PBMCs of each sample;
   (v) dividing the cancer antigen-reactive sub-population into microcultures;
   (vi) identifying a cancer antigen-reactive microculture; and
   (vii) expanding the microculture, thereby obtaining a clinical grade population of T cells specific for the cancer antigen, wherein the number of PBMCs of the cancer antigen-reactive sub-population identified in (iv) is less than about 10% of the number of PBMCs of (i).

2. The method of claim 1, wherein the method is carried out in less than about 7 weeks.

3. The method of claim 2, wherein the method is carried out in about 5 to about 6 weeks.

4. The method of claim 1, wherein (i) to (iv) is carried out within about 1 week.

5. The method of claim 1, wherein (i) to (vi) is carried out in about 30 days or less.

6. The method of claim 1, wherein the number of PBMCs of the antigen-reactive sub-population identified in (iv) is less than about 1% of the number of PBMCs of (i).

7. The method of claim 1, wherein the PBMCs are divided into about 96 sub-populations.

8. The method of claim 1, wherein about $3 \times 10^5$ PBMCs are contacted in (ii).

9. The method of claim 8, Wherein each sample of (iii) comprises about $1 \times 10^5$ PBMCs.

10. The method of claim 1, comprising contacting each sample of (iii) with an antigenic peptide presented by a carrier cell prior to (iv).

11. The method of claim 1, wherein the factor is Interferon-γ (IFN-γ).

12. The method of claim 1, wherein the cancer antigen is selected from the group consisting of gp100, NY-ESO-1, MART-1, MACE-A1, and mesothelin.

13. The method of claim 12, wherein the cancer antigen comprises an epitope selected from the group consisting of gp100₁₅₄₋₁₆₂ (SEQ ID NO: 2), NY-ESO-1₁₅₇₋₁₆₅ (SEQ ID NO: 6), MAGE-A1₂₇₈₋₂₈₆ (SEQ ID NO: 10), mesothelin₁₈₋₂₆ (SEQ ID NO: 11), and mesothelin₂₁₋₂₉ (SEQ ID NO: 12).

14. The method of claim 1, wherein the population of antigen-specific T cells obtained in (vii) is greater than about 90% clonal.

15. The method of claim 1, wherein the population of antigen-specific T cells obtained in (vii) is about 99% clonal.

16. The method of claim 1, wherein the antigen-specific T cells obtained in (vii) have high functional avidity for the antigen, recognize tumor cells expressing the antigen, and/or are CD27⁺.

17. The method of claim 16, wherein the antigen-specific T cells obtained in (vii) recognize target cells pulsed with about $10^{-10}$ to about $10^{-11}$ M antigen.

18. The method of claim 16, wherein at least 80% of the antigen-specific T cells obtained in (vii) are CD27⁺ T cells.

19. The method of claim 1, wherein the antigen-specific T cells obtained in (vii) are CD8+ T cells or CD4⁺ T cells.

\* \* \* \* \*

SEQUENCE LISTING

```
<160> NUMBER OF SEQ ID NOS: 20

<210> SEQ ID NO 1
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: amino acids 209-217 of gp100

<400> SEQUENCE: 1

Ile Thr Asp Gln Val Pro Phe Ser Val
1               5

<210> SEQ ID NO 2
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: amino acids 154-162 of gp100

<400> SEQUENCE: 2

Lys Thr Trp Gly Gln Tyr Trp Gln Val
1               5

<210> SEQ ID NO 3
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: amino acids 27-35 of MART-1

<400> SEQUENCE: 3

Ala Ala Gly Ile Gly Ile Leu Thr Val
1               5

<210> SEQ ID NO 4
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: amino acids 476-484 of HIV pol

<400> SEQUENCE: 4

Ile Leu Lys Glu Pro Val His Gly Val
1               5

<210> SEQ ID NO 5
<211> LENGTH: 9
<212> TYPE: PRT
<213> ORGANISM: Artificial
<220> FEATURE:
```

```
<223> OTHER INFORMATION: Synthetic
<220> FEATURE:
<221> NAME/KEY: MISC_FEATURE
<223> OTHER INFORMATION: amino acids 58-66 of FLU M1

<400> SEQUENCE: 5

Gly Ile Leu Gly Phe Val Phe Thr Leu
1               5

<210> SEQ ID NO 6
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: amino acids 157-165 of NY-ESO-1

<400> SEQUENCE: 6

Ser Leu Leu Met Trp Ile Thr Gln Cys
1               5

<210> SEQ ID NO 7
<211> LENGTH: 21
<212> TYPE: DNA
<213> ORGANISM: Artificial
<220> FEATURE:
<223> OTHER INFORMATION: Synthetic

<400> SEQUENCE: 7
agctctgcat cgttttgggt t                                        21

<210> SEQ ID NO 8
<211> LENGTH: 24
<212> TYPE: DNA
<213> ORGANISM: Artificial
<220> FEATURE:
<223> OTHER INFORMATION: Synthetic

<400> SEQUENCE: 8
gttccattat ccgctacatc tgaa                                     24

<210> SEQ ID NO 9
<211> LENGTH: 25
<212> TYPE: DNA
<213> ORGANISM: Artificial
<220> FEATURE:
<223> OTHER INFORMATION: Synthetic

<400> SEQUENCE: 9
tcttggctgt tactgccagg accca                                    25

<210> SEQ ID NO 10
<211> LENGTH: 9
<212> TYPE: PRT
<213> ORGANISM: Artificial
<220> FEATURE:
<223> OTHER INFORMATION: Synthetic

<400> SEQUENCE: 10

Lys Val Leu Glu Tyr Val Ile Lys Val
1               5

<210> SEQ ID NO 11
<211> LENGTH: 9
<212> TYPE: PRT
<213> ORGANISM: Artificial
```

<220> FEATURE:
<223> OTHER INFORMATION: Synthetic

<400> SEQUENCE: 11

Ser Leu Leu Phe Leu Leu Phe Ser Leu
1               5

<210> SEQ ID NO 12
<211> LENGTH: 9
<212> TYPE: PRT
<213> ORGANISM: Artificial
<220> FEATURE:
<223> OTHER INFORMATION: Synthetic

<400> SEQUENCE: 12

Phe Leu Leu Phe Ser Leu Gly Trp Val
1               5

<210> SEQ ID NO 13
<211> LENGTH: 9
<212> TYPE: PRT
<213> ORGANISM: Artificial
<220> FEATURE:
<223> OTHER INFORMATION: Synthetic

<400> SEQUENCE: 13

Asn Met Asn Gly Ser Glu Tyr Phe Val
1               5

<210> SEQ ID NO 14
<211> LENGTH: 9
<212> TYPE: PRT
<213> ORGANISM: Artificial
<220> FEATURE:
<223> OTHER INFORMATION: Synthetic

<400> SEQUENCE: 14

Val Leu Pro Leu Thr Val Ala Glu Val
1               5

<210> SEQ ID NO 15
<211> LENGTH: 9
<212> TYPE: PRT
<213> ORGANISM: Artificial
<220> FEATURE:
<223> OTHER INFORMATION: Synthetic

<400> SEQUENCE: 15

Leu Ile Phe Tyr Lys Lys Trp Glu Leu
1               5

<210> SEQ ID NO 16
<211> LENGTH: 9
<212> TYPE: PRT
<213> ORGANISM: Artificial
<220> FEATURE:
<223> OTHER INFORMATION: Synthetic

<400> SEQUENCE: 16

Leu Leu Ala Thr Gln Met Asp Arg Val
1               5

<210> SEQ ID NO 17
<211> LENGTH: 9
<212> TYPE: PRT
<213> ORGANISM: Artificial
<220> FEATURE:
<223> OTHER INFORMATION: Synthetic

```
<400> SEQUENCE: 17

Leu Leu Gly Phe Pro Cys Ala Glu Val
1               5

<210> SEQ ID NO 18
<211> LENGTH: 9
<212> TYPE: PRT
<213> ORGANISM: Artificial
<220> FEATURE:
<223> OTHER INFORMATION: Synthetic

<400> SEQUENCE: 18

Val Leu Leu Pro Arg Leu Val Ser Cys
1               5

<210> SEQ ID NO 19
<211> LENGTH: 9
<212> TYPE: PRT
<213> ORGANISM: Artificial
<220> FEATURE:
<223> OTHER INFORMATION: Synthetic

<400> SEQUENCE: 19

Leu Pro Leu Asp Leu Leu Leu Phe Leu
1               5

<210> SEQ ID NO 20
<211> LENGTH: 9
<212> TYPE: PRT
<213> ORGANISM: Artificial
<220> FEATURE:
<223> OTHER INFORMATION: Synthetic

<400> SEQUENCE: 20

Arg Leu Ser Glu Pro Pro Glu Asp Leu
1               5
```